(12) United States Patent
Fujimoto et al.

(10) Patent No.: US 7,202,364 B2
(45) Date of Patent: Apr. 10, 2007

(54) CERTAIN PHENYLACETIC ACIDS AND DERIVATIVES

(75) Inventors: Roger A. Fujimoto, Morristown, NJ (US); Leslie W. McQuire, Warren, NJ (US); Lauren G. Monovich, Summit, NJ (US); Benjamin B. Mugrage, Voorhees, NJ (US); David T. Parker, Livingston, NJ (US); John H. VanDuzer, Georgetown, MA (US); Sompong Wattanasin, Hopatcong, NJ (US)

(73) Assignee: Novartis, AG, Basel (CH)

( * ) Notice: Subject to any disclaimer, the term of this patent is extended or adjusted under 35 U.S.C. 154(b) by 65 days.

(21) Appl. No.: 10/724,457

(22) Filed: Nov. 25, 2003

(65) Prior Publication Data

US 2004/0132769 A1   Jul. 8, 2004

Related U.S. Application Data

(60) Provisional application No. 60/429,222, filed on Nov. 26, 2002.

(51) Int. Cl.
C07D 215/38 (2006.01)
C07D 215/44 (2006.01)
C07C 229/00 (2006.01)

(52) U.S. Cl. .................. 546/153; 546/157; 562/454; 562/456; 562/457

(58) Field of Classification Search ................ 562/454, 562/456, 457; 546/153, 167
See application file for complete search history.

(56) References Cited

U.S. PATENT DOCUMENTS

| | | |
|---|---|---|
| 3,531,493 A | 9/1970 | Gittos et al. |
| 3,558,690 A | 1/1971 | Sallmann et al. |
| 3,652,762 A | 3/1972 | Sallmann et al. |
| 3,895,063 A | 7/1975 | Sallmann et al. |
| 4,173,577 A | 11/1979 | Sallmann et al. |
| 4,548,952 A | 10/1985 | Cases |
| 5,068,250 A | 11/1991 | Penning et al. |
| 5,958,978 A | 9/1999 | Yamazaki et al. |
| 6,291,523 B1 | 9/2001 | Fujimoto et al. |
| 6,310,099 B1 * | 10/2001 | Fujimoto et al. ........... 514/567 |
| 6,355,680 B1 | 3/2002 | Cohen |
| 6,552,077 B2 | 4/2003 | Cohen |
| 6,649,629 B2 | 11/2003 | Bandarage et al. |

FOREIGN PATENT DOCUMENTS

| | | |
|---|---|---|
| DE | 3445011 A1 | 6/1985 |
| WO | WO 94/04484 | 3/1994 |
| WO | WO 96/00716 | 1/1996 |
| WO | WO 01/03684 | 1/2001 |
| WO | WO 01/23346 | 4/2001 |
| WO | WO 02/20090 | 3/2002 |
| WO | WO 02/78626 | 10/2002 |

OTHER PUBLICATIONS

Clish, C.B., Biochemical and Biophysical Research Communications, Vol. 288, pp. 868-874, 2001.*
Moser et al., "Synthesis and Quantitative Structure-Activity Relationships of Diclofenac Analogues", J.Med.Chem., vol. 33, pp. 2358-2368 (1990).
Wisenberg-Boettcher I. et al., Agents and Actions, "Pharmacological properties of five diclofenac metabolites identified in human plasma", vol. 34, No. 1/2 (1991).

* cited by examiner

Primary Examiner—D. Margaret Seaman
(74) Attorney, Agent, or Firm—Peter J. Waibel; Edward J. Wilusz, Jr.

(57) ABSTRACT

Compounds of formula (I)

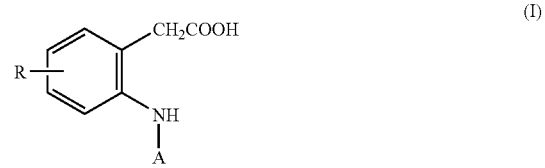

wherein
R is hydrogen, lower alkyl, ($C_3$–$C_6$)cycloalkyl, hydroxy, halo, lower alkoxy, trifluoromethoxy, trifluoromethyl or cyano; and
A is biaryl, optionally substituted β-naphthyl, bicyclic heterocyclic aryl, ($C_3$–$C_6$)cycloalkyl-monocyclic carbocyclic aryl, or ($C_5$ or $C_6$)cycloalkane fused-monocyclic carbocyclic aryl;
pharmaceutically acceptable salts thereof; and pharmaceutically acceptable esters thereof; which are useful for the treatment of COX-2 dependent disorders.

10 Claims, No Drawings

CERTAIN PHENYLACETIC ACIDS AND DERIVATIVES

This Application claims the benefit of Provisional Application No. 60/429,222 filed Nov. 26, 2002, which is incorporated herein by reference.

SUMMARY OF THE INVENTION

The invention relates to phenylacetic acids and derivatives as defined herein which are particularly potent and selective cyclooxygenase-2 (COX-2) inhibitors, methods for preparation thereof, pharmaceutical compositions comprising said compounds, methods of selectively inhibiting COX-2 activity and of treating conditions in mammals which are responsive to COX-2 inhibition using said compounds or pharmaceutical compositions comprising said compounds of the invention.

The present invention provides novel phenylacetic acids and derivatives which inhibit COX-2 without significantly inhibiting cyclooxygenase-1 (COX-1). The invention thus provides novel non-steroidal anti-inflammatory agents which are surprisingly free of undesirable side effects usually associated with the classical non-steroidal anti-inflammatory agents, such as gastrointestinal and renal side effects.

The compounds of the present invention are thus particularly useful or may be metabolically converted to compounds which are particularly useful as selective COX-2 inhibitors. They are thus particularly useful for the treatment of COX-2 dependent disorders in mammals, including inflammation, pyresis, pain, osteoarthritis, rheumatoid arthritis, dysmenorrhea, migraine headache, cancer (such as of the digestive tract, e.g., colon cancer and melanoma), neurodegenerative diseases (such as multiple sclerosis, Parkinson's disease and Alzheimer's disease), cardiovascular disorders (such as atherosclerosis, coronary artery disease and arteriosclerosis), osteoporosis, asthma, lupus and psoriasis while substantially eliminating undesirable gastrointestinal ulceration associated with conventional cyclooxygenase (COX) inhibitors. The compounds of the invention are also UV absorbers, in particular, UV-B absorbers, and are useful for blocking or absorbing UV radiation, for instance, for the treatment and prevention of sunburn, e.g., in suntan products.

Ocular applications of the compounds of the invention include the treatment of ocular inflammation, of ocular pain including pain associated with ocular surgery, such as PRK or cataract surgery, of ocular allergy, of photophobia of various etiology, of elevated intraocular pressure (in glaucoma) by inhibiting the production of trabecular meshwork inducible glucocorticoid response protein and of dry eye disease.

The compounds of the present invention are useful for the treatment of neoplasia particularly neoplasia that produce prostaglandins or express COX, including both benign and cancerous tumors, growths and polyps, in particular, epithelium cell-derived neoplasia. Compounds of the present invention are, in particular, useful for the treatment of liver, bladder, pancreatic, ovarian, prostate, cervical, lung and breast cancer and, especially gastrointestinal cancer, e.g., cancer of the colon, and skin cancer, e.g., squamous cell or basal cell cancers and melanoma, as indicated above.

The term "treatment" as used herein is to be understood as including both therapeutic and prophylactic modes of therapy, e.g., in relation to the treatment of neoplasia, therapy to prevent the onset of clinically or pre-clinically evident neoplasia, or for the prevention of initiation of malignant cells or to arrest or reverse the progression of pre-malignant to malignant cells, as well as the prevention or inhibition of neoplasia growth or metastasis. In this context, the present invention is, in particular, to be understood as embracing the use of compounds of the present invention to inhibit or prevent development of skin cancer, e.g., squamous or basal cell carcinoma consequential to UV light exposure, e.g., resulting from chronic exposure to the sun.

DETAILED DESCRIPTION OF THE INVENTION

The invention relates to compounds of formula (I)

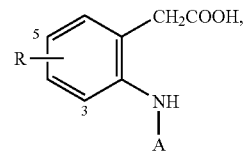

wherein
R is hydrogen, lower alkyl, $(C_3-C_6)$cycloalkyl, hydroxy, halo, lower alkoxy, trifluoromethoxy, trifluoromethyl or cyano; and A is biaryl, optionally substituted β-naphthyl, bicyclic heterocyclic aryl, $(C_3-C_6)$cycloalkylmonocyclic carbocyclic aryl, or $(C_5$ or $C_6)$cycloalkane fused-monocyclic carbocyclic aryl; provided that when bicyclic heterocyclic aryl is optionally substituted quinolinyl, R is located at the 5-position and R does not represent hydrogen;

pharmaceutically acceptable salts thereof; and pharmaceutically acceptable esters thereof.

Particular embodiments of the invention relate to compounds of formula (1), wherein A represents optionally substituted β-naphthyl, optionally substituted quinolinyl, optionally substituted isoquinolinyl, optionally substituted 5,6,7,8-tetrahydronaphthyl, optionally substituted indanyl, optionally substituted biphenylyl, optionally substituted $(C_3-C_6)$cycloalkylphenyl or optionally substituted monocyclic heteroaryl-phenyl; provided that when A is optionally substituted quinolinyl, R is located at the 5-position and R does not represent hydrogen; pharmaceutically acceptable salts thereof; and pharmaceutically acceptable esters thereof.

A more particular embodiment of the invention relates to the compounds of formula (II)

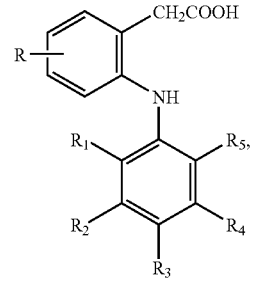

wherein
R is hydrogen, $(C_1-C_4)$alkyl, $(C_3-C_6)$cycloalkyl, halo, lower alkoxy, trifluoromethoxy, cyano or trifluoromethyl;
$R_1$ is hydrogen, fluoro, chloro, $(C_1$ or $C_2)$alkyl or trifluoromethyl;
$R_2$ is hydrogen, fluoro, chloro, $(C_1$ or $C_2)$alkyl or trifluoromethyl;
$R_3$ is optionally substituted phenyl or $(C_3-C_6)$cycloalkyl;
$R_4$ is hydrogen, halo, lower alkyl or trifluoromethyl; and
$R_5$ is halo, lower alkyl or trifluoromethyl;

pharmaceutically acceptable salts thereof; and pharmaceutically acceptable esters thereof.

In the compounds of formulae (I) and (II), R is preferably located at the 5-position of the ring.

A more particular embodiment of the invention relates to the compounds of formula (II), wherein
R is hydrogen, methyl, ethyl, propyl, methoxy, chloro, fluoro, cyclopropyl, cyano, trifluoromethoxy or trifluoromethyl;
$R_1$, $R_2$, $R_4$ and $R_5$ are, independently, hydrogen, fluoro or chloro; and
$R_3$ is $(C_3-C_6)$cycloalkyl, phenyl, or phenyl mono- or poly-substituted independently by lower alkyl, fluoro, chloro, lower alkoxy or $(C_1$ or $C_2)$alkylenedioxy;

pharmaceutically acceptable salts thereof; and pharmaceutically acceptable esters thereof.

Another particular embodiment of the invention relates to the compounds of formula (III)

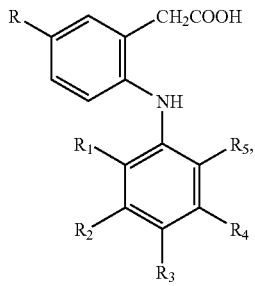

(III)

wherein
R is hydrogen, $(C_1-C_4)$alkyl, $(C—C_6)$cycloalkyl, halo, lower alkoxy, trifluoromethoxy or trifluoromethyl;
$R_1$ is hydrogen, chloro, fluoro or $(C_1$ or $C_2)$alkyl;
$R_2$ is hydrogen or fluoro;
$R_3$ is cyclopropyl, cyclohexyl, phenyl or phenyl substituted by chloro, fluoro, lower alkoxy, lower alkyl or lower alkylenedioxy;
$R_4$ is hydrogen, $(C_1$ or $C_2)$alkyl, trifluoromethyl or fluoro; and
$R_5$ is fluoro, chloro or $(C_1$ or $C_2)$alkyl;

pharmaceutically acceptable salts thereof; and pharmaceutically acceptable esters thereof.

A further embodiment of the invention relates to the compounds of formula (III), wherein
R is $(C_1$ or $C_2)$-alkyl, cyclopropyl, chloro or fluoro;
$R_1$ is chloro or fluoro;
$R_2$ is hydrogen or fluoro;
$R_3$ is cyclopropyl;

$R_4$ is hydrogen, methyl or fluoro; and
$R_5$ is fluoro;

pharmaceutically acceptable salts thereof; and pharmaceutically acceptable esters thereof.

Another aspect of the invention relates to the compounds of formula (I), wherein
R is hydrogen, lower alkyl, $(C_2-C_6)$cycloalkyl, halo, lower alkoxy, trifluoromethoxy, cyano or trifluoromethyl; and
A is selected from radicals (a) and (b)

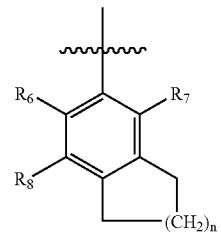

(a)

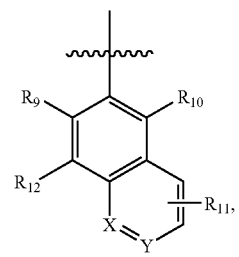

(b)

wherein in radical (a)
n is 1 or 2; and
$R_6$–$R_8$ are, independently, hydrogen, lower alkyl, lower alkoxy, trifluoromethyl or halo; and
wherein in radical (b)
$R_9$–$R_{12}$ are, independently, hydrogen, lower alkyl, lower alkoxy, trifluoromethyl or halo; and
X and Y are CH, or one of the X and Y is N and the other is CH; provided that when X is N and Y is CH, R is located at the 5-position and R does not represent hydrogen;

pharmaceutically acceptable salts thereof; and pharmaceutically acceptable esters thereof.

Preferably at least one of $R_6$ and $R_7$ and one of $R_9$ and $R_{10}$ is lower alkyl or halo.

A further embodiment of the invention relates to the compounds of formula (IIIa)

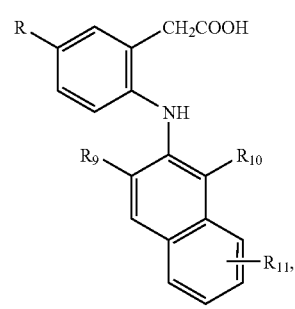

(IIIa)

wherein
R is lower alkyl, cyclopropyl, chloro or fluoro;
R$_9$ is hydrogen, chloro or fluoro;
R$_{10}$ is chloro or fluoro; and
R$_{11}$ is fluoro, chloro or lower alkoxy;

pharmaceutically acceptable salts thereof; and pharmaceutically acceptable esters thereof.

In the above compounds of formulae (I), (II), (III) and (IIIa), R is preferably methyl, ethyl, propyl, cyclopropyl, chloro or fluoro, most preferably chloro, methyl, ethyl or cyclopropyl.

The general definitions used herein have the following meaning within the scope of the present invention, unless otherwise indicated.

Pharmaceutically acceptable esters are preferably prodrug ester derivatives which are convertible by solvolysis or under physiological conditions to the free carboxylic acids of, e.g., formula (I). Such esters are, e.g., lower alkyl esters, such as the methyl or ethyl ester; carboxy-lower alkyl esters, such as the carboxymethyl ester; nitrooxy- or nitrosooxy-lower alkyl esters, such as the 4-nitrooxybutyl or 4-nitrosooxybutyl ester; and the like. Preferred are the phenylacetoxyacetic acids of formula (Ia)

wherein R and A have meaning as defined hereinabove for compounds of formulae (I)–(IIIa); and pharmaceutically acceptable salts thereof.

Pharmaceutically acceptable salts represent metal salts, such as alkaline metal salts, e.g., sodium, potassium, magnesium or calcium salts; as well as ammonium salts, which are formed, e.g., with ammonia and mono- or di-alkylamines, such as diethylammonium salts; and with amino acids, such as arginine and histidine salts.

A lower alkyl group contains up to 7 carbon atoms, preferably 1–4 carbon atoms, may be straight chain or branched and represents, e.g., methyl, ethyl, propyl, butyl, isopropyl, isobutyl and the like, preferably methyl or ethyl. Lower alkoxy is methoxy, ethoxy and the like.

Biaryl represents two directly linked monocyclic aryl groups which are, independently, either carbocyclic or heterocyclic.

Biaryl for A in formula (I) represents monocyclic carbocyclic aryl substituted by monocyclic carbocyclic aryl, namely biphenylyl, advantageously 3- or 4-biphenylyl, optionally substituted on one or both benzene rings by one or more of lower alkyl, halo, hydroxy, lower alkoxy, trifluoromethoxy, lower alkylenedioxy and trifluoromethyl, advantageously wherein at least one substituent is ortho to the point of attachment of the NH group. Biaryl also represents monocyclic carbocyclic aryl substituted by heterocyclic aryl, namely optionally substituted monocyclic heteroarylphenyl, preferably phenyl substituted in the meta- or para-position by, e.g., thiazolyl, thienyl, pyridyl, oxazolyl or isoxazolyl, in which one or both rings are optionally substituted by one or more substituents selected from lower alkyl, halo and trifluoromethyl, advantageously at least one said substituent being ortho to the point of attachment of the NH group.

Optionally substituted β-naphthyl for A in formula (I) is 2-naphthyl optionally substituted at one or both of the 1- and 3-positions by, e.g., halo, lower alkyl or trifluoromethyl, and further optionally substituted, e.g., at the 6- or 7-position by halo, lower alkyl, lower alkoxy, trifluoromethyl or hydroxy.

Bicyclic heterocyclic aryl for A in formula (I) is preferably quinolinyl or isoquinolinyl, each being optionally substituted by one or more substituents independently selected from, e.g., halo, lower alkyl, lower alkoxy and trifluoromethyl.

(C$_3$–C$_6$)Cycloalkyl-monocyclic carbocyclic aryl for A in formula (I) is phenyl substituted, preferably in the para or meta position, by (C$_3$–C$_6$)cycloalkyl, e.g., cyclopropyl, cyclopentyl or cyclohexyl, and further optionally substituted by one or more (1–4) substituents independently selected from, e.g., lower alkyl, lower alkoxy, halo and trifluoromethyl, advantageously at least one said substituent being ortho to the point of attachment of the —NH group.

(C$_3$–C$_6$)Cycloalkyl is cyclopropyl, cyclobutyl, cyclopentyl or cyclohexyl, preferably cyclopropyl. (C$_5$ or C$_6$)Cycloalkane fused-monocarbocyclic aryl for A in formula (I) is preferably 5-indanyl or (2- or 3-)5,6,7,8-tetrahydronaphthyl, each being optionally substituted on the benzene ring thereof by one or more substituents independently selected from, e.g., halo, lower alkyl, lower alkoxy and trifluoromethyl.

Monocyclic carbocyclic aryl is optionally substituted phenyl, e.g., phenyl or phenyl substituted by 1–5 substituents independently selected from, e.g., lower alkyl, halo, trifluoromethyl and lower alkoxy.

Monocyclic heteroaryl is 5- or 6-membered heteroaryl, which contains 1 or 2 heteroatoms selected from oxygen, nitrogen and sulfur, and represents preferably thiazolyl, thienyl, pyridyl, pyrimidinyl, oxazolyl or isoxazolyl optionally substituted by, e.g., lower alkyl or halo.

Halo is preferably chloro, bromo or fluoro, advantageously chloro or fluoro.

Optionally substituted quinolinyl is quinolinyl or quinolinyl substituted by, e.g., lower alkyl, halo, lower alkoxy or trifluoromethyl.

Optionally substituted isoquinolinyl is isoquinolinyl or isoquinolinyl substituted by, e.g., lower alkyl, halo, lower alkoxy or trifluoromethyl.

Optionally substituted 5,6,7,8-tetrahydronaphthyl is 5,6,7,8-tetrahydronaphthyl or 5,6,7,8-tetrahydronaphthyl substituted on the phenyl ring by, e.g., lower alkyl, halo, lower alkoxy or trifluoromethyl.

Optionally substituted indanyl is indanyl or indanyl substituted on the phenyl ring by, e.g., lower alkyl, halo, lower alkoxy or trifluoromethyl.

Optionally substituted biphenylyl is preferably 3- or 4-biphenylyl or 3- or 4-biphenylyl substituted on one or both benzene rings by one or more substituents independently selected from, e.g., lower alkyl, lower alkoxy, halo and trifluoromethyl.

Optionally substituted (C$_3$–C$_6$)cycloalkylphenyl is phenyl substituted by, e.g., cyclopropyl, cyclopentyl or cyclohexyl, advantageously in the para position, in which the phenyl ring is further optionally substituted by 1–4 substituents independently selected from, e.g., lower alkyl, halo, lower alkoxy and trifluoromethyl.

The compounds of the invention are useful as selective COX-2 inhibitors or as prodrugs thereof. The selective COX-2 inhibitors and prodrugs thereof of the invention are particularly useful for the treatment of, e.g., inflammation, pyresis, pain, osteoarthritis, dysmenorrhea, rheumatoid arthritis and other conditions responsive to the inhibition of COX-2 and are typically substantially free of undesirable gastrointestinal side effects associated with conventional non-steroidal anti-inflammatory agents.

The above-cited properties are demonstrable in vitro and in vivo tests using advantageously mammals, e.g., rats, mice, dogs, monkeys and isolated cells or enzyme preparations of human and non-human origin. Said compounds can be applied in vitro in the form of solutions, e.g., aqueous solutions, and in vivo advantageously orally, topically or parenterally, e.g., intravenously. The dosage in vitro may range from about $10^{-5}$–$10^{-9}$ molar concentrations. The dosage in vivo may range, depending on the route of administration, between about 1 mg/kg and 100 mg/kg.

The biological properties can be demonstrated in tests well-known in the art, e.g., as described in U.S. Pat. No. 6,291,523, and as described herein.

COX-2 inhibition is determined in an enzymatic in vitro assay using a commercially available kit (Cayman Chemical Company).

The test compound (stock solution in DMSO diluted with buffer to various concentrations) is pre-incubated with 30–50 units of purified recombinant human COX-2 and hemactin (1 µM) for 30 minutes at 25° C., followed by incubation with 100 µM arachidonic acid and the colorimetric substrate TMPD (N,N,N',N'-tetramethyl-p-phenylenediamine) for 5–7 minutes at 25° C., followed by calorimetric detection of oxidized TMPD at 590 nm. The COX-2 activity in the presence of test compound is compared to COX-2 activity for control without test compound.

COX inhibition is also determined in vitro using cellular assays for inhibition of both COX-1 and COX-2.

Cellular assays for testing COX inhibitors are well-known in the art and based on the fact that the COX enzyme (prostaglandin H synthase) catalyzes the rate limiting step in prostaglandin synthesis from arachidonic acid. Two enzymes mediate the reaction: COX-1 is a constitutive form of the enzyme whereas COX-2 is induced in response to various growth factors and cytokines.

In vitro COX-1 and COX-2 inhibition is determined in the cell-based assays in order to assess the in vitro activity and selectivity for COX-2 inhibition, using a prostaglandin $E_2$ immunoassay (Cayman $PGE_2$ Kit). The cells utilized are HEK-293 EBNA cells that have been transfected and have a stable expression of either recombinant human COX-1 or recombinant human COX-2, respectively. Cells are plated out into 96-well plates in which the assay is performed. Both cell lines are pre-treated with compound dilutions for 30 minutes at 37° C., then arachidonic acid (1 µM) is added as exogenous substrate. The supernatant is harvested 15 minutes later and the production of $PGE_2$ is measured by immunoassay. For $IC_{50}$ determinations, compounds are tested at 5–9 concentrations in singlet, duplicate or quadruplicate replicates at each concentration (highest concentration 30 µM). The mean inhibition of $PGE_2$ (compared to cells not treated with compound) for each concentration is calculated, a plot is made of mean % inhibition versus log compound concentration, and the $IC_{50}$ value calculated using a 4-parameter logistic fit. The relative effects on each enzyme are compared to assess selectivity for inhibition of COX-2.

In vitro COX-1 and COX-2 inhibition is also determined in human whole blood where COX-1 is constitutively expressed in platelets and COX-2 expression is induced in mononuclear cells by treatment with lipopolysaccharide (LPS) (10 µg/mL). For this assay heparinized human blood is divided into two aliquots: one for measuring $TxB_2$ production (a surrogate indicator of COX-1 activity) and a second for measuring $PGE_2$ production (a surrogate for COX-2 activity). The blood samples are pretreated with test compounds for one hour before stimulation. Compounds are tested in a final concentration range from 0.1 nM to 300 µM using half log increases in concentrations. To measure inhibition of thromboxane $B_2$ ($TxB_2$) generation, A23187 (50 µM) is added, and the blood incubated for one hour. $PGE_2$ production is measured after the addition of LPS (10 µg/mL) followed by overnight incubation. After incubation with A23187 or LPS the samples are centrifuged at 250×g for 10 minutes at 4° C. to collect serum. The amounts $PGE_2$ and $TxB_2$ present in the serum are measured using a chemiluminesence enzyme immunoassay from Assay Designs Inc. (Ann Arbor, Mich.). The levels of prostaglandin in each sample are normalized to the percent inhibition caused by each concentration of the test compound. The percent inhibition data for each donor is pooled and fitted to a 4-parameter logistic function using a regression.

$IC_{50}$ values for compounds of formula (I) in the COX-2 inhibition assays are as low as about 0.010 µM. Preferred are compounds for which the ratio of $IC_{50}$ values for COX-1 and COX-2 inhibition is above 50, advantageously in the range of about 100–1000 or higher.

The inhibition of prostaglandin-$E_2$ production produced by COX-2 is determined in vivo in the lipopolysaccharide (LPS)-challenged subcutaneous air pouch model in the rat. See *Advances in Inflammation Research*, Raven Press (1986); *J. Med. Chem.*, Vol. 39, p. 1846 (1996); *J. Pathol.*, Vol. 141, pp. 483–495; and *J. Pathol.*, Vol. 134, pp. 147–156.

Female Lewis rats are anesthetized and then dorsal air pouches are prepared by subcutaneous injection of 10 mL of air through a sterile 0.45 micron syringe-adapted filter. Six or 7 days after preparation, the air pouches are injected with LPS (5 µg per pouch) suspended in sterile phosphate buffered saline. Compounds for evaluation are administered by gavage one hour prior to or two or more hours after LPS challenge. The pouch contents are harvested five hours after LPS challenge and $PGE_2$ levels present in the pouch fluids are measured by enzyme immunoassay. Illustrative of the invention, the compound of Example 4(j) inhibits $PGE_2$ formation by about 50% at 1 mg/kg p.o.

The in vivo inhibition of thromboxane $B_2$ ($TXB_2$) produced by COX-1 is measured ex vivo in the serum of rats after oral administration of compound.

Briefly, male Sprague Dawley rats are fasted overnight, administered compound in fortified cornstarch vehicle by gavage and sacrificed by carbon dioxide inhalation 30 minutes to eight hours later. Blood is collected by cardiac puncture into tubes without anti-coagulant, allowed to clot and serum is separated by centrifugation. Serum is stored frozen for later analysis of $TXB_2$ by radioimmunoassay. Each experiment contains the following groups (5–6 rats per group): vehicle control and test compounds, either at different doses or different time points. $TXB_2$ data is expressed as a percentage of the levels measured in the vehicle control group.

Anti-inflammatory activity is determined using the carrageenan-induced rat paw edema assay following a modification of the procedure of Offerness et al., described in: *Nonsteroidal Antiinflammatory Drugs*, Lombardino, Ed., John Wiley & Sons, pp. 116–128 (1986).

Sprague Dawley rats (200–225 g) are fasted overnight, then orally dosed with the compound suspended in a fortified cornstarch solution. After one hour, a 0.1 mL volume of 1% carrageenan in saline is injected into the sub-plantar region of the left hind paw which causes an inflammatory response. At three hours post-carrageenan, the rats are euthanized and both hind paws are cut off at the paw hair line and weighed on an electronic balance. The amount of edema in the inflamed paw is determined by subtracting the weight of the non-inflamed paw (right) from the weight of the inflamed paw (left). The percent inhibition by the compound is determined for each animal as the percent paw weight gained as compared to the control average.

Illustrative of the invention, the compounds of Examples 4(b) and 4(j) inhibit carrageenan-induced edema at 30 mg/kg p.o.

The gastric tolerability assay is used to assess gross ulceration in the rat, measured four hours after oral administration of the test compound. The test is carried out as follows:

Male Sprague Dawley rats are fasted overnight, administered compound in fortified cornstarch vehicle by gavage and sacrificed by carbon dioxide inhalation four hours later. The stomachs are removed and gross gastric lesions counted and measured to give the total lesion length per rat. Each experiment contains the following groups (5–6 rats per group): vehicle control, test compounds and diclofenac as a reference compound.

Data are calculated as the mean number of ulcers in a group, the mean length of ulcers (mm) in the group and as the ulcer index (UI).

$$UI = \text{mean length of ulcers in a group} \times \text{ulcer incidence}$$

where ulcer incidence is the fraction of animals in the group with lesions (100% incidence is 1).

Illustrative of the invention, the compounds of Examples 4(b) and 4(j) are essentially free of any gastric ulcerogenic effect at 30 mg/kg p.o.

Intestinal tolerability can be determined by measuring the effect on intestinal permeability. Lack of increase in permeability is indicative of intestinal tolerability.

The method used is a modification of a procedure by Davies et al., Pharm. Res., Vol. 11, pp. 1652–1656 (1994) and is based on the fact that excretion of orally administered $^{51}$Cr-EDTA, a marker of small intestinal permeability, is increased by NSAIDs. Groups of male Sprague Dawley rats ($\geq$12 per group) are administered a single, oral dose of test compound or vehicle by gastric intubation. Immediately following compound dose, each rat is administered $^{51}$Cr-EDTA (5 µCi per rat) by gastric intubation. The rats are placed in individual metabolic cages and given food and water ad libitum. Urine is collected over a 24-hour period. Twenty-four hours after administration of $^{51}$Cr-EDTA the rats are sacrificed. To quantify compound effect on intestinal permeability, the excreted $^{51}$Cr-EDTA measured in the urine of compound-treated rats is compared to the excreted $^{51}$Cr-EDTA measured in the urine of vehicle-treated rats. Relative permeability is determined by calculating the activity present in each urine sample as a percent of the administered dose after correcting for background radiation.

The analgesic activity of the compounds of the invention is determined using the well-known Randall-Selitto assay.

The Randall-Selitto paw pressure assay measures antinociception (analgesic activity) in inflamed tissue by comparing the pressure threshold in the inflamed paw of the rat after oral administration of test drug with that in the inflamed paw of rats administered corn starch vehicle orally.

Groups of 10 male Wistar rats weighing 40–50 g are fasted overnight prior to testing. Hyperalgesia is induced by the injection of 0.1 mL of a 20% suspension of Brewer's yeast with a 26-gauge needle into the sub-plantar region of the right hind paw. The left paw is not injected and is used as the control paw for determination of hyperalgesia. Vehicle (fortified corn starch suspension 3%) at 10 mL/kg, reference compound (diclofenac is run in every experiment at the same dose as test compounds) and test compounds at different doses suspended in vehicle at 10 mL/kg are administered orally two hours after the yeast injection. The threshold for paw withdrawal is quantified with a Basile Analgesymeter one hour after oral administration of test compounds. The nociceptive threshold is defined as the force in grams at which the rat withdraws its foot or vocalizes. Either vocalization or foot withdrawal is recorded as a response.

The data are analyzed by comparing the mean pain threshold of the corn starch vehicle-treated group for the inflamed and non-inflamed paws to that of individual drug-treated rats. Individual rats in the drug-treated groups and positive control (diclofenac) group are called reactors if the individual pain threshold in each paw exceeds the control group mean threshold by two standard deviations of that mean. The mean pain thresholds of the inflamed paw in the control group are compared to the individual pain thresholds of the inflamed paw in the test drug group. The non-inflamed control mean pressure threshold is compared to the non-inflamed individual pressure thresholds in the test groups. Results are expressed as number of reactors in each test group (n=10) for inflamed and non-inflamed paws. Percentages are calculated by dividing number of reactors by total number of rats used for a compound.

The anti-arthritic effect of the compounds of the invention can be determined in the well-known chronic adjuvant arthritis test in the rat.

Ocular effects can be demonstrated in well-known ophthalmic assay methods.

Similarly anti-tumor activity can be demonstrated in well-known anti-tumor animal tests.

The compounds of formula (I) can be prepared, e.g., (a) by coupling a compound of formula (IV) or (IVa)

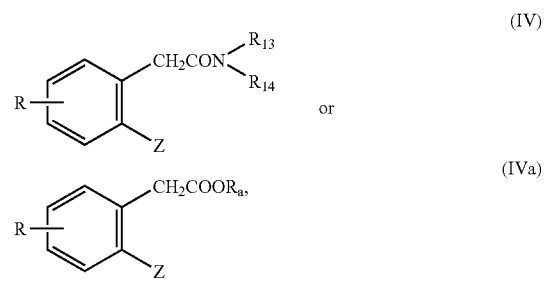

wherein

Z is iodo or bromo;

R has meaning as defined above;

$R_a$ is hydrogen, an alkali metal cation or lower alkyl, preferably isopropyl; and $R_{13}$ and $R_{14}$ are lower alkyl; or $R_{13}$ and $R_{14}$ together with the nitrogen atom represent piperidino, pyrrolidino or morpholino;

with a compound of formula (V)

$$A\text{—}NH_2 \tag{V}$$

wherein A has meaning as defined above in the presence of copper and cuprous iodide to obtain a compound of formula (VI) or (VIa)

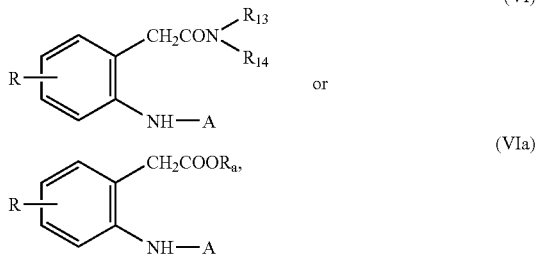

and hydrolyzing the resulting compound of formula (VI) or (VIa) to a compound of formula (I); or (b) for compounds in which R represents alkyl, e.g., ethyl at the 5-position, by condensing a compound of formula (VII)

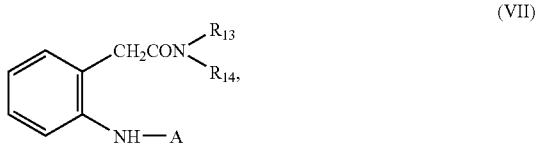

wherein A has meaning as defined herein, with a reactive functional derivative of, e.g., acetic acid, such as acetyl chloride, in a Friedel-Crafts acylation to reaction to obtain a compound of the formula (VIII)

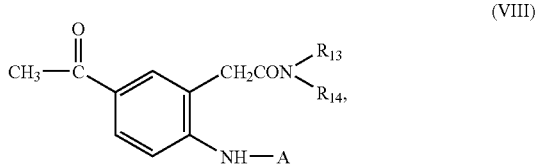

wherein A has meaning as defined herein which is in turn hydrogenolyzed and then hydrolyzed to obtain a compound of formula (I), wherein R represents, e g., ethyl; or (c) by hydrolyzing a lactam of formula (IX)

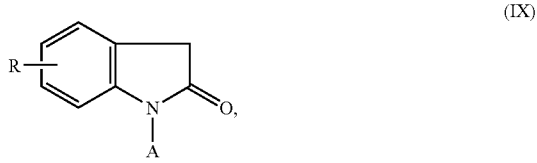

wherein R and A have meaning as defined herein, with a strong base; and in above processes, if desired, temporarily protecting any interfering reactive groups and then isolating the resulting compound of the invention; and, if desired, converting any resulting compound into another compound of the invention; and/or if desired converting a free carboxylic acid of the invention into a pharmaceutically acceptable ester derivative thereof; and/or if desired, converting a resulting free acid into a salt or a resulting salt into the free acid or into another salt.

In starting compounds and intermediates, which are converted to the compounds of the invention in a manner described herein, functional groups present, such as amino, hydroxy and carboxyl groups, are optionally protected by conventional protecting groups that are common in preparative organic chemistry. Protected hydroxy, amino and carboxyl groups are those that can be converted under mild conditions into free amino, hydroxy and carboxyl groups without other undesirable side reactions taking place. For example, hydroxy protecting groups are preferably benzyl or substituted benzyl groups, or acyl groups, such as pivaloyl.

The preparation of compounds of formulae (VI) and (Via) according to process (a) is carried out under conditions of a modified Ullmann condensation for the preparation of diarylamines, e.g., in the presence of copper powder and copper (I) iodide and potassium carbonate, optionally in an inert high boiling solvent, such as nitrobenzene, toluene, xylene or N-methylpyrrolidone, at elevated temperature, e.g., in the range of 100–200° C., preferably at reflux temperature, according to general methodology described by Nohara, *Chem Abstr*, Vol. 94, p. 15402x(1951); and Moser et al., *J Med Chem*, Vol. 33, p. 2358 (1990). When Z is bromo, the condensation is carried out in the presence of an iodide salt, e.g., potassium iodide.

Hydrolysis of the resulting ortho-anilinophenylacetamides of formula (VI) is carried out in aqueous alkali hydroxide, e.g., in 6N NaOH in the presence of an alcohol, e.g., ethanol, propanol and butanol, at elevated temperature, such as reflux temperature of the reaction mixture.

The hydrolysis of esters of formula (VIa) is carried out according to methods known in the art, e.g., under basic conditions as described above for the compounds of formula (VI) or alternatively under acidic conditions, e.g., using methanesulfonic acid.

The starting materials of formula (IV) or (IVa) are generally known or can be prepared using methodology known in the art, e.g. as described by Nohara in Japanese Patent Application No. 78/96,434 (1978); U.S. Pat. No. 6,291,523 and as illustrated herein.

For example, the corresponding anthranilic acid is converted to the ortho-diazonium derivative followed by treatment with an alkali metal iodide in acid, e.g., sulfuric acid, to obtain the 2-iodobenzoic acid or lower alkyl ester thereof. Reduction to the corresponding benzyl alcohol, e.g., with diborane or lithium aluminum hydride for the ester, conversion of the alcohol first to the bromide and then to the nitrite, hydrolysis of the nitrite to the acetic acid and conversion to the N,N-dialkylamide according to methodology known in the art yields a starting material of formula (IV).

Alternatively, e.g., the starting material of formula (IV), wherein Z is Br and R is cyclopropyl can be prepared by first condensing according to the method outlined in *J. Am. Chem. Soc.*, Vol. 123, p. 4155 (2001), e.g., 2-bromo-5-iodobenzoic acid methyl ester with cyclopropyl bromide in the presence of indium trichloride to obtain 2-bromo-5-cyclopropylbenzoic acid methyl ester which is converted as described above to the corresponding 2-bromo-5-cyclopropylphenylacetamide of formula (IV).

Furthermore, the starting materials of formula (IV), wherein R is, e.g., ethyl, can be prepared by Friedel-Crafts acetylation of oxindole with, e.g., acetyl chloride in the presence of aluminum chloride, reduction of the resulting ketone by, e.g., catalytic hydrogenolysis, followed by hydrolytic cleavage of the resulting 5-ethyloxindole to the ortho amino-phenylacetic acid. Diazotization in the presence of, e.g., potassium iodide yields the ortho iodo-phenylacetic acid which is converted to an amide of formula (IV).

Esters of formula (IVa) are prepared from the corresponding acids according to esterification methods known in the art.

The amines of formula (V) are either known in the art or are prepared according to methods well-known in the art or as illustrated herein.

For example, the biarylamines are prepared by condensation under conditions of a palladium catalyzed Suzuki coupling reaction of, e.g., an appropriately substituted 4-bromoaniline with an appropriately substituted phenylboronic acid.

Similarly, e.g., cyclopropyl substituted anilines are prepared from the corresponding bromo substituted anilines (as the free amine or in protected form) by palladium catalyzed condensation with cyclopropyl boronic acid, according to methodology in *Tetrahedron Letters*, Vol. 43, p. 6987 (2002), and as illustrated in the examples.

Alternatively, 4-cycloalkyl substituted anilines are prepared by condensation of a 4-iodo or bromo substituted aniline protected, e.g., as a phthalimide derivative with, e.g., cyclopropyl bromide in the presence of indium trichloride followed by removal of the protecting group, similarly to general methodology in *J Am Chem Soc*, Vol. 123, p. 4155 (2001).

The preparation of, e.g., 5-ethyl or 5-n-propyl substituted compounds according to process (b) is carried out under conditions of Friedel-Crafts acylation, e.g., in the presence of aluminum chloride in an inert solvent, such as 1,2-dichloroethane, followed by hydrogenolysis, e.g., using palladium on charcoal catalyst, preferably in acetic acid as solvent, at room temperature and about 3 atmospheres pressure.

The starting materials of formula (VII) are prepared generally as described under process (a) starting with an amide of formula (IV) in which R represents hydrogen, e.g., as described in Moser et al. (1990), supra.

The preparation of the compounds of the invention according to process (c) can be carried out under conditions known in the art for the hydrolytic cleavage of lactams, preferably with a strong aqueous base, such as aqueous sodium hydroxide, optionally in the presence of an organic water miscible solvent, such as methanol at elevated temperature in the range of about 50–100° C., as generally described in U.S. Pat. No. 3,558,690.

The oxindole starting materials are prepared by N-acylation of a diarylamine of the formula (X)

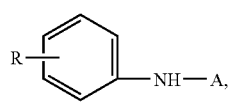
(X)

wherein R and A have meaning as defined above with a haloacetyl chloride, preferably chloroacetyl chloride, advantageously at elevated temperature, e.g., near 100° C., to obtain a compound of the formula (XI)

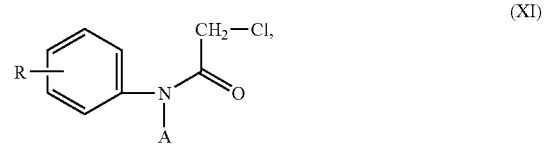
(XI)

wherein R and A have meaning as defined hereinabove. Cyclization of a compound of formula (XI) is carried out under conditions of Friedel-Crafts alkylation in an inert solvent, such as dichlorobenzene, in the presence of Friedel-Crafts catalysts, e.g., aluminum chloride and ethylaluminum dichloride, at elevated temperature, e.g., at 120–175° C.

The stating amines of formula (X) can be prepared by an Ullmann condensation and other methods known in the art, e.g., a Buchwald coupling reaction.

Esters of the carboxylic acids of formula (I) are prepared by condensation of the carboxylic acid, in the form of a salt or in the presence of a base, with a halide (bromide or chloride) corresponding to the esterifying alcohol, such as benzyl chloroacetate, according to methodology well-known in the art, e.g., in a polar solvent, such as N,N-dimethylformamide, and if required further modifying the resulting product. For example, if the esterification product is itself an ester, such can be converted to the carboxylic acid, e.g., by hydrogenolysis of a resulting benzyl ester. Also if the esterification product is itself a halide, such can for instance be converted to the nitrooxy derivative by reaction with, e.g., silver nitrate.

For example, the compounds of formula (Ia) are preferably prepared by condensing a salt of a carboxylic acid of formula (I) above with a compound of formula $$X-CH_2-COOR_b,$$

wherein

X is a leaving group; and $R_b$ is a carboxy-protecting group to obtain a compound of formula (Ia) in carboxyprotected form, and subsequently removing the protecting group $R_b$.

The esterification can be carried under esterification conditions known in the art, e.g., in a polar solvent, such as N,N-dimethylformamide, at a temperature range of room temperature to about 100° C., preferably at a range of 40–60° C.

The salt of the acid of formula (I) is preferably an alkali metal salt, e.g., the sodium salt which may be prepared in situ.

Leaving group X is preferably halo, e.g., chloro or bromo, or lower alkylsulfonyloxy, e.g., methanesulfonyloxy.

Carboxy-protecting group $R_b$ is preferably benzyl.

The resulting benzyl esters can be converted to the free acids of formula (Ia) preferably by hydrogenolysis with hydrogen in the presence of, e.g., Pd/C catalyst in acetic acid at atmospheric pressure or under Parr hydrogenation at a temperature ranging from room temperature to about 50° C.

The invention includes any novel starting materials and processes for their manufacture.

Finally, compounds of the invention are either obtained in the free form, or as a salt thereof if salt forming groups are present.

The acidic compounds of the invention may be converted into metal salts with pharmaceutically acceptable bases, e.g., an aqueous alkali metal hydroxide, advantageously in the presence of an ethereal or alcoholic solvent, such as a lower alkanol. Resulting salts may be converted into the free compounds by treatment with acids. These or other salts can also be used for purification of the compounds obtained. Ammonium salts are obtained by reaction with the appropriate amine, e.g., diethylamine, and the like.

Compounds of the invention having basic groups can be converted into acid addition salts, especially pharmaceutically acceptable salts. These are formed, e.g., with inorganic acids, such as mineral acids, e.g., sulfuric acid, a phosphoric or hydrohalic acid; or with organic carboxylic acids, such as $(C_1-C_4)$alkanecarboxylic acids which, e.g., are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid; or with organic sulfonic acids, such as $(C_1-C_4)$alkylsulfonic acids, e.g., methanesulfonic acid; or arylsulfonic acids which are unsubstituted or substituted, e.g., by halogen. Preferred are salts formed with hydrochloric acid, methanesulfonic acid and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal, topical and parenteral administration to mammals, including man, to inhibit COX-2-activity, and for the treatment of COX-2 dependent disorders, and comprise an effective amount of a pharmacologically active compound of the invention, either alone or in combination with other therapeutic agents, and one or more pharmaceutically acceptable carriers.

More particularly, the pharmaceutical compositions comprise an effective COX-2 inhibiting amount of a selective COX-2 inhibiting compound of the invention which is substantially free of COX-1 inhibiting activity and of side effects attributed thereto.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, sodium carboxymethylcellulose and/or polyvinylpyrrolidone; if desired
  d) disintegrants, e.g., starches, agar, alginic acid or its sodium salt, or effervescent mixtures; and/or
  e) absorbents, colorants, flavors and sweeteners.

Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1–75%, preferably about 1–50%, of the active ingredient.

Tablets may be either film coated or enteric coated according to methods known in the art.

Suitable formulations for transdermal application include an effective amount of a compound of the invention with carrier. Advantageous carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable formulations for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. In this regard it is noted that compounds of the present invention are capable of absorbing UV rays in the range of 290–320 nm while allowing passage of tanning rays at higher wavelengths. They are thus particularly suited for use in topical, including cosmetic, formulations well-known in the art. Such may contain solubilizers, stabilizers, tonicity enhancing agents, buffers and preservatives. Formulations suitable for topical application can be prepared, e.g., as described in U.S. Pat. No. 4,784,808. Formulations for ocular administration can be prepared, e.g., as described in U.S. Pat. Nos. 4,829,088 and 4,960,799.

The compounds of the invention may be used alone or in conjunction with other therapeutic agents. For example, suitable additional active agents for use in relation to the treatment of neoplasia (malignant and benign) include, e.g., the anti-neoplastic agents or radioprotective agents recited in International Patent Application WO 98/16227 and the like. Other suitable additional therapeutic agents include analgesic agents, such as oxycodone, codeine, tramadol, levorphanol, propoxyphene, ketorolac, pentazocine, meperidine and the like; also anti-platelet agents, such as aspirin, clopidogrel, ticlopidine and the like; also bisphosphonates, such as zoledronate, pamidronate, risedronate, alendronate and the like; also statins, such as fluvastatin, atorvastatin, lovastatin, simvastatin, rosuvastatin, pitavastatin and the like.

In conjunction with another active ingredient, a compound of the invention may be administered either simultaneously, before or after the other active ingredient, either separately by the same or different route of administration or together in the same pharmaceutical formulation.

The dosage of active compound administered is dependent on the species of warm-blooded animal (mammal), the body weight, age and individual condition, and on the form of administration. A unit dosage for oral administration to a mammal of about 50–70 kg may contain between about 5 mg and 500 mg, of the active ingredient.

The present invention also relates to methods of using the compounds of the invention and their pharmaceutically acceptable salts, or pharmaceutical compositions thereof, in mammals for inhibiting COX-2 and for the treatment of conditions as described herein, e.g., inflammation, pain, rheumatoid arthritis, osteoarthritis, dysmenorrheal, tumors and other COX-2-dependent disorders.

Particularly, the present invention relates to a method of selectively inhibiting COX-2 activity in a mammal without substantially inhibiting COX-1 activity, which comprises administering to a mammal in need thereof an effective COX-2 inhibiting amount of a compound of the invention.

Thus, the present invention also relates to a method of treating COX-2 dependent disorders in mammals, which comprises administering to a mammal in need thereof an effective COX-2 inhibiting amount of a compound of the invention.

More particularly, the present invention relates to a method of treating COX-2 dependent disorders in mammals while substantially eliminating undesirable side effects associated with COX-1 inhibiting activity which comprises administering to a mammal in need thereof an effective COX-2 inhibiting amount of a selective COX-2 inhibiting compound of the invention which is substantially free of COX-1 inhibiting activity.

More specifically, such relates to a method of, e.g., treating rheumatoid arthritis, osteoarthritis, pain, dysmenorrhea or inflammation in mammals without causing undesirable gastrointestinal ulceration, which method comprises administering to a mammal in need thereof a correspondingly effective amount of a compound of the invention.

The following examples are intended to illustrate the invention and are not to be construed as being limitations thereon. Temperatures are given in degrees Centigrade. If not mentioned otherwise, all evaporations are performed under reduced pressure, preferably between about 15 mm Hg and 100 mm Hg (=20–133 mbar). The structure of final products, intermediates and starting materials is confirmed by standard analytical methods, e.g., microanalysis and spectroscopic characteristics, e.g., MS, IR, NMR. Abbreviations used are those conventional in the art.

Abbreviations
BOC: t-butoxycarbonyl
DME: 1,2-Dimethoxyethane
DMF: N,N-dimethylformamide
DPPA: Diphenylphosphoryl azide
EDCI: 1-(3-dimethylaminopropyl)-3-ethylcarbodiimide hydrochloride
HOAt: 1-hydroxy-7-azabenzotriazole
LAH: lithium aluminum hydride
NBS: N-bromosuccinimide
NCS: N-chlorosuccinimide
NMM: N-methylmorpholine
THF: tetrahydrofuran
TLC: thin layer chromatography

EXAMPLES

Example 1

Aniline Starting Materials

A. 2,3,5,6-Tetrafluoro-4-phenylaniline 2,3,5,6-Tetrafluoroaniline (25.0 g, 0.15 mol) is dissolved in methanol (100 mL) and treated with elemental bromine (28.4 g, 0.17 mol) by dropwise addition at room temperature. Solid sodium bicarbonate (15 g, 0.18 mol) is added portionwise and the resulting mixture stirred for an additional 2 hours. The reaction mixture is partitioned between $Et_2O$ (500 mL) and water (1000 mL). The organic layer is dried ($MgSO_4$) and evaporated by a rotary evaporator to give 2,3,5,6-tetrafluoro-4-bromoaniline (m.p. 59–60° C.).

2,3,5,6-Tetrafluoro-4-bromoaniline (13.8 g, 56.7 mmol) is dissolved in benzene (200 mL) and treated with 1.5 equivalents of phenylboronic acid (10.4 g, 85.1 mmol) and a catalytic amount of tetrakistriphenylphosphine palladium(0) (4.2 g, 3.6 mmol) as a solution in ethanol (30 mL). Sodium carbonate (60 mL of 2 M aqueous solution) is added and the reaction mixture stirred and heated to reflux temperature for 24 hours. After cooling to room temperature the mixture is partitioned between $Et_2O$ (500 mL) and water (250 mL). The organic layer is washed with brine, dried ($MgSO_4$) and concentrated by rotary evaporator. The residual oil is purified by flash chromatography (9:1 hexanes/EtOAc) to give 2,3,5,6-tetrafluoro-4-phenylaniline as an oil.

$^1$H-NMR: ($CDCl_3$) 7.43 (m, 5H, ArH), 4.05 (s, 2H, $NH_2$).

B. 2,6-Dichloro-4-phenylaniline

The preparation is an adaptation of Brewster, *Org. Synth. II*, p. 347 (1943).

2,6-Dichloroaniline (16.2 g, 0.1 mol) is suspended in a solution of sodium bicarbonate (8.6 g, 0.1 mol in 100 mL of water) and warmed to 60° C. Elemental iodine (25.4 g, 0.1 mol) is added portionwise and the resulting mixture stirred at 60° C. for 3 days. After cooling to room temperature, the reaction mixture is partitioned between $CH_2Cl_2$ (250 mL) and saturated sodium bisulfite solution (500 mL). The aqueous layer is re-extracted with additional $CH_2Cl_2$ (250 mL) and the combined organic layers dried ($MgSO_4$) and concentrated by rotary evaporator. The residual oil is purified by flash chromatography (9:1 hexanes/EtOAc) to give 2,6-dichloro-4-iodoaniline (m.p. 100–102° C.).

2,6-Dichloro-4-iodoaniline (10.4 g, 36.0 mmol) is dissolved in toluene (100 mL) and treated with 1.5 equivalents of phenylboronic acid (6.6 g, 54 mmol), and a catalytic amount of tetrakistriphenylphosphine palladium(0) (3.0 g, 2.6 mmol) as a solution in ethanol (20 mL). Sodium carbonate (40 mL of 2 M aqueous solution) is added and the reaction mixture stirred and heated to reflux temperature for 24 hours. After cooling to room temperature, the mixture is partitioned between $Et_2O$ (300 mL) and water (150 mL). The organic layer is washed with brine, dried ($MgSO_4$) and concentrated by rotary evaporator. The residual oil is purified by flash chromatography (9:1 hexanes/EtOAc) to give 2,6-dichloro-4-phenylaniline (m.p. 112–113° C.).

C. 2-Fluoro-4-phenyl-6-chloroaniline

2-Fluoro-6-chloroaniline (28.8 g, 0.2 mol) is suspended in a solution of sodium bicarbonate (17.2 g, 0.2 mol in 150 mL water) and warmed to 60° C. Elemental iodine (50.8 g, 0.2 mol) is added portionwise and the resulting mixture stirred at 60° C. for 3 days. After cooling to room temperature, the reaction mixture is partitioned between $CH_2Cl_2$ (350 mL) and saturated sodium bisulfite solution (500 mL). The aqueous layer is re-extracted with additional $CH_2Cl_2$ (250 mL) and the combined organic layers dried ($MgSO_4$) and concentrated by rotary evaporator. The residual oil is purified by flash chromatography (9:1 hexanes/EtOAc) to give 2-fluoro-4-iodo-6-chloroaniline (m.p. 85–87° C.).

2-Fluoro-4-iodo-6-chloroaniline (8.0 g, 36.0 mmol) is dissolved in DMF (110 mL) and treated with 2.8 equivalents of phenylboronic acid (10.0 g, 82 mmol), and a catalytic amount of tetrakistriphenylphosphine palladium(0) (3.0 g, 2.6 mmol) as a solution in DMF (20 mL). Sodium carbonate (30 mL of 2 M aqueous solution) is added and the reaction mixture stirred and heated to 100° C. for 24 hours. After cooling to room temperature most of the DMF is removed by rotary evaporator under high vacuum. The residual brown oil is partitioned between Et₂O (300 mL) and water (150 mL). The organic layer is washed with brine, dried (MgSO₄) and concentrated by rotary evaporator. The residual oil is purified by flash chromatography (9:1 hexanes/EtOAc) to give 2-fluoro-4-phenyl-6-chloroaniline (m.p. 105–107° C.).

D. 2,3,5,6-Tetrafluoro-4-(3'-methoxyphenyl)aniline (i) 2,3,5,6-Tetrafluoro-4-bromoaniline (7.5 g, 30.7 mmol) is dissolved in DME (150 mL) and treated with 3-methoxyphenylboronic acid (4.7 g, 30.7 mmol), a catalytic amount of tetrakistriphenylphosphine palladium(0) (0.70 g, 0.6 mmol) and triphenylphosphine (0.66 g, 2.5 mmol). Potassium carbonate (8.5 μg in 50 mL of water) is added and the reaction mixture stirred and heated to 90° C. for 24 hours. After cooling to room temperature most of the DME is removed by rotary evaporator under high vacuum. The resulting material is partitioned between EtOAc (200 mL) and water (250 mL). The organic layer is washed with brine, dried (Na₂SO₄) and concentrated by rotary evaporator. The crude reaction product is purified by flash chromatography (9:1 hexanes/EtOAc, then 6:4 hexanes/EtOAC) to give 2,3,5,6-tetrafluoro-4-(3'-methoxyphenyl)aniline (m.p. 94–96° C.).

(ii) Alternative procedure: 2,3,5,6-Tetrafluoro-4-bromoaniline (12.0 g, 49.2 mmol) is dissolved in DME (250 mL) and treated with 3-methoxyphenylboronic acid (7.5 g, 49.2 mmol), a catalytic amount of palladium(II) acetate (0.23 g, 1.0 mmol) and tri-o-tolylphosphine (1.22 g, 4.0 mmol). Potassium carbonate (13.6 g in 50 mL water) is added and the reaction mixture stirred, purged with nitrogen, then heated to 90° C. for 24 hours. After cooling to room temperature most of the DME is removed by rotary evaporator under high vacuum. The resulting material is partitioned between EtOAc (200 mL) and water (250 mL). The organic layer is washed with brine, dried (Na₂SO₄) and concentrated by rotary evaporator. The crude reaction product is purified by flash chromatography (9:1 hexanes/EtOAc, then 6:4 hexanes/EtOAc) to give 2,3,5,6-tetrafluoro-4-(3'-methoxyphenyl)aniline (m.p. 94–96° C.).

E. 2-Fluoro-4-(4'-fluorophenyl)aniline

2-Fluoro-4-bromoaniline (10.7 g), 4-fluorophenylboronic acid (11.9 g), 60 mL of 2 N NaOH and 200 mL of benzene are combined and degassed with N₂. Palladium tetrakistriphenylphosphine (4.2 g) is added and the mixture stirred at reflux temperature overnight. After cooling, the reaction is filtered through Celite and concentrated. The oily residue is purified by flash chromatography (5–10% EtOAc/hexane) to afford 2-fluoro-4-(4'-fluorophenyl)aniline as a solid.

F. 2-Chloro-4-cyclohexylaniline

The preparation is an adaptation of Altau et al., *J Chem Eng Data*, Vol. 8, p. 122 (1963).

4-Cyclohexylaniline (20 g, 114 mmol) is dissolved in acetic acid (50 mL) and stirred with acetic anhydride (12 g, 114 mol). The reaction is exothermic and the mixture is allowed to cool to room temperature, then stirred for 2 additional hours. The volatiles are removed by rotary evaporator and the residual solid triturated with hexane and filtered to give 4-cyclohexylacetanilide (m.p. 126–128° C.).

4-Cyclohexylacetanilide (24 g, 110 mmol) is dissolved in a mixture of concentrated HCl (25 mL) and acetic acid (75 mL). The mixture is cooled in an ice bath and a solution of sodium chlorate (NaClO₃, 7.5 g, 70 mmol) in water (30 mL) is added via a dropping funnel. The reaction is allowed to warm to room temperature and then poured into saturated sodium bisulfite solution (500 mL). The solid which forms is isolated by filtration and subsequently washed first with water (500 mL) and then a mixture of hexanes/Et2O (10:1, 500 mL). The resulting solid is air dried to yield 2-chloro-4-cyclohexylacetanilide (m.p. 110–112° C.).

Hydrolysis in a 1:1 mixture of concentrated HCl and ethanol at reflux temperature for 12 hours yields 2-chloro-4-cyclohexylaniline.

G. 2-Chloro-4-cyclopropylaniline

2-Chloro-4-iodoaniline (12.65 g) and phthalic anhydride (7.4 g) are dissolved in 30 mL of dimethylformamide. The solution is heated to reflux for 16 hours. The reaction mixture is diluted with diethyl ether and washed with brine to yield a precipitate which is filtered off and washed with water and diethyl ether to yield N-(2-chloro-4-iodophenyl) phthalimide as a white solid.

The above iodide is reacted with cyclopropyl bromide and InCl₃ according to method outlined in *J Am Chem Soc*, Vol. 123, p. 4155 (2001), to yield N-(2-chloro-4-cyclopropylphenyl)phthalimide.

The above phthalimide (3.9 g) in 80 mL of methanol is treated with 1.9 mL of anhydrous hydrazine. The reaction mixture is refluxed for 1.5 hours then cooled to room temperature and concentrated in vacuo to a paste. This paste is diluted with diethyl ether and filtered. The filtrate is concentrated in vacuo to give 2-chloro-4-cyclopropylaniline as a viscous oil.

Similarly prepared are, e.g., 2-chloro-6-fluoro-4-cyclopropylaniline from 2-chloro-6-fluoro-4-iodoaniline and 2-fluoro-4-cyclopropylaniline from 2-fluoro-4-iodoaniline.

H. 1-Chloro-2-aminonaphthalene

A solution of 2-naphthylamine (1.43 g, 10 mmol) and triethylamine (1.11 g, 11 mmol) in 10 mL of CH₂Cl₂ is cooled to 0° C. under an atmosphere of nitrogen. To this solution is added dropwise a solution of acetyl chloride (0.86 g, 11 mmol) in 10 mL of CH₂Cl₂. The mixture is allowed to warm to room temperature and stirred overnight. The mixture is concentrated in vacuo and then 1 N HCl is added to the residue to bring the mixture to pH 4. The mixture is extracted 3 times with 20 mL of EtOAc and the combined organic layers are washed with 20 mL each of H₂O, saturated aqueous NaHCO₃ and saturated brine. The organic layer is dried over MgSO₄, filtered and the solvents are removed in vacuo to give 2-acetylaminonaphthalene as a solid which is used without further purification. A solution of NaClO₃ in (0.33 g, 30 mmol) in 0.77 mL of H₂O is added dropwise to a mixture of 1.0 g of 2-acetylaminonaphthalene in 5 mL of concentrated HCl and 6 mL of HOAc at 0° C. The mixture is allowed to warm to room temperature and stirred overnight under an atmosphere of nitrogen. The mixture is poured over 20 g of ice and is extracted three times with 20 mL of CH₂Cl₂. The combined organic layers are washed with 20 mL each of water, saturated aqueous sodium bicarbonate and saturated brine, and dried over magnesium sulfate. The mixture is filtered and the solvents are removed in vacuo to give an oil which is purified by flash chromatography on silica gel (CH₂Cl₂) to give 1-chloro 2-acetylaminonaphthalene as a solid. A mixture of 0.17 g (0.77 mmol) of 1-chloro 2-acetylaminonaphthalene in 3.9 mL of 6 N HCl is heated to 85° C. and is stirred for 8 hours. The mixture is cooled to 0° C. and solid Na₂CO₃ is carefully added to bring the mixture to pH 8. The mixture is extracted 3 times with 20 mL of CH₂Cl₂. The combined organic layers are washed with 15 mL of saturated brine, dried over Na₂SO₄ and the solvents are removed in vacuo to give 1-chloro 2-aminonaphthalene as a solid.

I. 6-Chloro-5-aminoindane

A solution of 5-aminoindane (8.6 g, 64.6 mmol) and triethylamine (1.11 g, 11 mmol) in 50 mL of 1,4-dioxane is cooled to 0° C. under an atmosphere of nitrogen. To this solution is added dropwise acetic anhydride (15.6 g, 139 mmol). The mixture is allowed to warm to room temperature and stirred overnight. The mixture is poured onto 200 g of ice and stirred for 1 hour. The precipitate is filtered off, washed with $H_2O$ and dried in vacuo to give 5-acetylaminodoindane. The product is dissolved in 33.1 mL of HOAc and 26.9 mL of concentrated HCl and the mixture is stirred at room temperature under an atmosphere of nitrogen. An aqueous solution of $NaClO_3$ (3.51 g, 32.8 mmol) is added slowly dropwise and the mixture is stirred overnight. The mixture is poured onto 200 g of ice, stirred for 1 hour, filtered and the product is dried in vacuo to give 6-chloro-5-acetylaminoindane. A mixture of 2.6 g (12.4 mmol) of this solid in 70 mL of concentrated HCl is heated to reflux for 6 hours under an atmosphere of nitrogen. The mixture is cooled to 0° C. and filtered. The solids are washed with ice water and the filtrate is adjusted to pH 8 by carefully adding solid $NaHCO_3$. The mixture is extracted 4 times with 50 mL of $CH_2Cl_2$. The combined organic layers are washed with 50 mL of saturated brine, dried over $MgSO_4$, filtered and the solvents are removed in vacuo to give 6-chloro-5-aminoindane.

J. 6-Methyl-5-aminoindane

A solution of 7.18 g (54 mmol) of 5-aminoindane and 10.9 g (108 mmol) of triethylamine in 40 mL of $CH_2Cl_2$ is cooled to 5° C. Acetic anhydride (7.63 g, 81 mmol) is added carefully dropwise. The reaction is allowed to warm to room temperature and stirred overnight. The reaction is poured into 1 N HCl to acidify it and is then extracted with EtOAc. The organic layer is evaporated in vacuo. Toluene is added to the residue and the mixture is evaporated in vacuo to give 5-acetylaminoindane that was used without purification. 5-Acetylaminoindane (8.8 g) is dissolved in a solution of 26 mL of HOAc and 126 mL of acetic anhydride, and cooled to 0° C. Nitric acid (8.3 mL) is added carefully dropwise to the solution so as to control the temperature of the exothermic reaction. The mixture is stirred for an additional 30 minutes and is poured onto ice and filtered. The solid is washed with water and dried in a vacuum oven overnight to give 5-acetylamino-6-nitroindane that is used without further purification. A mixture of this solid in 230 mL of 6 N HCl is heated to reflux for 4 hours. The mixture is neutralized with $Na_2CO_3$ (152 g) in 1000 mL of $H_2O$. The solids are filtered and dried overnight in a vacuum oven to give 5-amino-6-nitroindane.

5-Amino-6-nitroindane (4 g) is dissolved in 10 mL of MeOH, 30 mL of $H_2O$ and 20 mL of $H_2SO_4$, and cooled to 0° C. A solution of 1.72 g of $NaNO_2$ (24.9 mmol) in 5 mL of $H_2O$ is added dropwise, keeping the temperature of the reaction below 8° C. The mixture is allowed to stir for 30 minutes. This mixture is then added dropwise to a mixture of CuBr (1.8 g, 12.5 mmol) and 6 mL of 48% HBr in 30 mL of $H_2O$ that is heated to 60° C. The reaction is cooled and added to $H_2O$ and EtOAc. The organic layer is separated and the solvents evaporated in vacuo to give a residue that is purified by silica gel chromatography (75% hexane/EtOAc) to give 5-bromo-6-nitroindane. A mixture of this indane (2.59 g, 12.2 mmol), 4.88 g (27.2 mmol) of tetramethyltin, 0.1 g of $Pd(OAc)_2$ (0.45 mmol), 0.3 g (O-tol)$_3$P (0.98 mmol), 7 mL of $Et_3N$ and 7 mL of DMF is heated in a sealed tube to 65° C. for 3 days. The mixture is acidified with 1 N HCl and extracted with EtOAc. The organic layer is washed with saturated brine and dried over $Na_2SO_4$ and the solvents are evaporated in vacuo to give a residue that is purified by column chromatography (80% hexane/EtOAc) to give 5-methyl-6-nitroindane. To a mixture of 1.3 mL of HOAc and 7.3 mL of $H_2O$ heated to 90° C. is added 2.22 g of Fe. The mixture is heated until the gas evolution subsides. A solution of 1.9 g of 5-methyl-6-nitroindane (10.7 mmol) in 50 mL of EtOH is added dropwise and the reaction is heated to reflux for 30 minutes. The mixture is extracted twice with $CH_2Cl_2$. The combined organic layers are washed with saturated brine and dried over $Na_2SO_4$ and the solvents evaporated in vacuo to give a residue that is purified by column chromatography (75% hexane EtOAc) to give 6-methyl-5-aminoindane (also named 5-methyl-6-aminoindane).

K. 4-Cyclopropyl-2-fluoro-3-trifluoromethylaniline

4-Bromo-2-fluoro-3-trifluoromethylaniline is prepared from 2-fluoro-3-trifluoromethylaniline by treatment with NBS in DMF according to the procedure described in International Application WO 94/18179.

2-Fluoro-3-trifluoromethylaniline (28.8 g, 161 mmol) is dissolved in DMF (100 mL). A solution of NBS (28.6 g, 161 mmol) in DMF (100 mL) is added dropwise at room temperature. After 3 hours, the reaction is diluted with $Et_2O$ and washed with brine. The separated organic phase is dried ($Na_2SO_4$) and concentrated to give 4-bromo-2-fluoro-3-trifluoromethylaniline as an oil.

4-Cyclopropyl-2-fluoro-3-trifluoromethylaniline is prepared from 4-bromo-2-fluoro-3-trifluoromethylaniline by palladium-catalyzed coupling to cyclopropylboronic acid, similarly to the method outlined in *Tetrahedron Letters*, Vol. 43, p. 6987 (2002).

4-Bromo-2-fluoro-3-trifluoromethylaniline (5.0 g, 19.4 mmol), cyclopropylboronic acid (2.16 g, 25.2 mmol), $K_3PO_4$ (14.4 g, 67.8 mmol) and tricyclohexyl phosphine (0.54 g, 1.9 mmol) are dissolved in toluene (80 mL) and water (4 mL). The solution is degassed with $N_2$, heated to 90° C., and $Pd(OAc)_2$ (0.22 g, 1.0 mmol) is added. The reaction is heated at 90° C. for 5 hours, cooled, diluted with $Et_2O$, filtered, washed with brine, dried ($Na_2SO_4$) and concentrated in vacuo. The residue is purified by column chromatography (EtOAc/hexanes) to give 4-cyclopropyl-2-fluoro-3-trifluoromethylaniline.

Similarly prepared are 4-cyclopropyl-2-fluoro-5-trifluoromethylaniline and 4-cyclopropyl-2,6-difluoroaniline.

L. 4-Cyclopropyl-3,5-difluoro-2-chloroaniline 3,5-Difluoroaniline (10.0 g, 77.5 mmol) is dissolved in DMF (100 mL). NBS (13.9 g, 78.0 mmol) is added portionwise at room temperature. After stirring overnight at room temperature, the reaction mixture is diluted with $Et_2O$ and washed with brine. The separated organic phase is dried ($Na_2SO_4$) and concentrated to give an oil which is purified by column chromatography (methylene chloride/hexanes) to give 4-bromo-3,5-difluoroaniline.

4-Bromo-3,5-difluoroaniline (10.5 g, 50.5 mmol) is dissolved in DMF (100 mL). NCS (28.6 g, 50.5 mmol) is added portionwise at room temperature. After 48 hours, the reaction is diluted with $Et_2O$ and washed with brine. The separated organic phase is dried ($Na_2SO_4$) and concentrated to give an oil. The residue is purified by column chromatography (EtOAc/hexanes) to give 4-bromo-2-chloro-3,5-difluoroaniline.

A mixture of 4-bromo-2-chloro-3,5-difluoroaniline (5.35 g, 22.0 mmol), cyclopropylboronic acid (2.20 g, 24.0 mmol), $K_3PO_4$ (16 g, 78 mmol) and tricyclohexyl phosphine (0.623 g, 2.24 mmol) in toluene (30 mL) and water (8 mL) is degassed with $N_2$ and heated to 100° C. $Pd(OAc)_2$ (0.25 g, 1.16 mmol) is added. The reaction mixture is heated to 100° C. overnight, cooled and loaded directly on a column of silica gel. The residue is purified by column chromatography (EtOAc/hexanes) to give 4-cyclopropyl-3,5-difluoro-2-chloroaniline.

M. 2-Chloro-4-cyclopropyl-5-methyl-6-fluoroaniline

2-Chloro-5-methyl-6-fluorobenzoic acid (43 g, 0.25 mol) is suspended in $CH_2Cl_2$ (500 mL) and treated with thionyl chloride (36 mL, 0.49 mol) by dropwise addition, immediately followed by the addition of several drops (0.1 mL) of DMF. The mixture is heated to reflux temperature and stirred for 12 hours during which time the solid completely dissolves and a clear solution is obtained. After cooling to room temperature, most of the solvent is removed by rotary evaporator and toluene (500 mL) is added. The solution is again concentrated by rotary evaporator to remove residual thionyl chloride. The light yellow oil that results is filtered through a plug of cotton and dissolved in $CH_2Cl_2$ (1000 mL). The organic layer is washed with brine (500 mL), dried ($MgSO_4$) and concentrated by rotary evaporator. The white solid, which results, is triturated with hexanes/$Et_2O$ (4:1, 500 mL) and collected to provide 2-chloro-5-methyl-6-fluorobenzamide as a white solid (m.p. 151–153° C.).

A solution of sodium methoxide is generated by treating metallic sodium (29 g, 1.26 mol) with 1000 mL of anhydrous methanol by dropwise addition under an inert atmosphere. After the metal is completely consumed, the solution is heated at reflux temperature for 30 minutes and then cooled to room temperature. 2-Chloro-5-methyl-6-fluorobenzamide (42 g, 0.22 mol) is added and stirring continued for an additional 30 minutes at room temperature. N-Bromosuccinimide (78 g, 0.44 mol) is then slowly added via a powder additional funnel. The reaction mixture is warmed to 60° C. for 3 hours during which time foaming is observed. The reaction mixture is cooled to room temperature and most of the solvent is removed by rotary evaporator. The residue is partitioned between EtOAc (1000 mL) and water (1000 mL). The organic layer is separted and washed with water (500 mL) and then brine (2×500 mL). The organic layer is dried ($MgSO_4$), filtered and concentrated by rotary evaporator the crude product is then purified using flash chromatography, eluting with 4:1 hexanes/EtOAc to give N-(2-chloro-5-methyl-6-fluorophenyl)-carbamic acid methyl ester as a white solid (m.p. 109–112° C.).

N-(2-chloro-5-methyl-6-fluorophenyl)-carbamic acid methyl ester (39 g, 0.18 mmol) is dissolved in MeOH (150 mL), water (150 mL) and 30% NaOH solution (150 mL). The reaction mixture is heated to reflux temperature for 3 days and then cooled to room temperature. The reaction is concentrated by rotary evaporator to remove most of the methanol and then partitioned between $Et_2O$ (500 mL) and water (500 mL). The aqueous phase is extracted again with $Et_2O$ (250 mL) and the combined organic layers washed with brine (500 mL), dried and concentrated by rotary evaporator. The crude product is purified by bulb-to-bulb distillation to give 2-chloro-5-methyl-6-fluoroaniline as a colorless oil (b.p. 120–131° C. at ~20 mm of Hg), which forms a white crystalline solid upon storage at 4° C.

2-Chloro-5-methyl-6-fluoroaniline (23 g, 0.14 mol) and N-bromosuccinimide (25 g, 0.14 mol) are dissolved with stirring in 200 mL of anhydrous DMF. The reaction mixture is stirred overnight and then most of the DMF is removed by rotary evaporator under high vacuum. The dark brown residue is partitioned between 1:1 Et2O/hexane (500 mL) and water (500 mL). The organic layer is washed with brine (5×250 mL), dried ($MgSO_4$) and concentrated by rotary evaporator. The crude material is purified using flash chromatography (20% $CH_2Cl_2$/hexanes) and then further purified by bulb-to-bulb distillation (b.p. 155–165° C. at ~20 mm of Hg) to give 2-chloro-4-bromo-5-methyl-6-fluoroaniline as a peach-colored solid which is re-crystallized from ice-cold hexanes (m.p. 67–71° C.).

2-Chloro-4-bromo-5-methyl-6-fluoroaniline (6.5 g, 27 mmol), cyclopropylboronic acid (2.8 g, 33 mmol), tetrakis (triphenylphosphine)palladium (0) (1.4 g, 1.3 mmol), potassium phosphate (20.2 g, 95 mmol) and tricyclohexylphosphine (0.77 g, 2.7 mmol) are combined and stirred in 200 mL of a 4:1 DME/water solution. The mixture is degassed by repeated alternating application of vacuum and positive nitrogen pressure (10×). The mixture is heated to reflux temperature for 2 days and then cooled to room temperature. Most of the DME is removed by rotary evaporator and the residual mixture is partitioned between $Et_2O$ (250 mL) and water (250 mL). The organic phase is washed with brine (3×250 mL), dried ($MgSO_4$) and concentrated by rotary evaporator. The crude product is purified using flash chromatography (8% $CH_2Cl_2$/hexanes) to give 2-chloro-4-cyclopropyl-5-methyl-6-fluoroaniline as a tan oil.

N. 2-Chloro-5-cyclopropyl-6-fluoroaniline

The preparation is an adaptation of a method described in *Tetrahedron Lett*, Vol. 37, p. 6551 (1996).

A solution of lithium diiosopropyl amide is generated by adding n-BuLi (360 mL of 2 M solution in THF) to diisopropylamine (73 g, 0.722 mol) in 500 mL of anhydrous THF while a reaction temperature of −60° C. is maintained by cooling in dry-ice acetone bath. After stirring for 30 minutes, 1-bromo-4-chloro-2-fluorobenzene (75 g, 0.36 mol) is added and stirring maintained at −70° C. for 2 hours. The cold solution is then transferred, via a cannula, under an inert atmosphere to a suspension of solid $CO_2$ (100 g, excess) in anhydrous $Et_2O$. The mixture is allowed to warm to room temperature with stirring and then the solvent removed by rotary evaporator. The residual solid is treated with 1 N HCl solution until pH=3.0 and the mixture is filtered. The white solid that is obtained is suspended in 1000 mL of 2 N HCl solution and stirred for an additional 1 hour. The suspension is filtered to collect a white solid which is air dried, suspended in 100 mL of hexanes and collected to give 2-chloro-5-bromo-6-fluorobenzoic acid.

2-Chloro-5-bromo-6-fluorobenzoic acid (91 g, 0.36 mol) is suspended in $CH_2Cl_2$ (200 mL) and treated with oxalyl chloride (51 g, 0.40 mol) by dropwise addition, immediately followed by the addition of several drops (0.1 mL) of DMF. The mixture is stirred at room temperature for 3 hours during which time the solid completely dissolves and a clear solution is obtained. The solvent is removed by rotary evaporator and the residue is added to 1000 mL of ammonium hydroxide while stirring at 0° C. The product is collected by filtration and washed with water to give 2-chloro-5-bromo-6-fluorobenzamide as a white solid.

A solution of sodium methoxide is generated by treating metallic sodium (18 g, 0.78 mol) with 1000 mL of anhydrous methanol by dropwise addition under an inert atmosphere.

After the metal is completely consumed the solution is heated at reflux temperature for 30 minutes and then cooled to room temperature. 2-Chloro-5-bromo-6-fluorobenzamide (65 g, 0.26 mol) is added and stirring continued for an additional 30 minutes at room temperature. N-Bromosuccinimide (92 g, 0.52 mol) is then slowly added via a powder addition funnel. The reaction mixture is warmed to 60° C. for 30 minutes during which time foaming is observed. The reaction mixture is cooled to room temperature and most of the solvent is removed by rotary evaporator. The residue is partitioned between EtOAc (1000 mL) and water (1000 mL). The organic layer is separated and washed with water (5×500 mL) and then brine (2×500 mL). The organic layer is dried (MgSO$_4$), filtered and concentrated by rotary evaporator to give N-(2-chloro-5-bromo-6-fluorophenyl)-carbamic acid methyl ester as a light yellow solid (m.p. 107–112° C.).

N-(2-chloro-5-bromo-6-fluorophenyl)-carbamic ester methyl ester (8.65 g, 30.6 mmol), cyclopropylboronic acid (3.16 g, 36.7 mmol), potassium phosphate (22.8 g, 107 mmol), palladium acetate (343 mg, 1.53 mmol) and tricyclohexylphosphine (858 mg, 3.06 mmol) are combined and stirred in a two-phase solution comprised of toluene (350 mL) and water (75 mL). The mixture is degassed by repeated alternating application of vacuum and positive nitrogen pressure (10×). The mixture is heated to 95° C. for 4 days and then cooled to room temperature. The reaction mixture is partitioned between EtOAc (500 mL) and water (500 mL). The organic phase is washed with water (2×250 mL), brine (500 mL) and then dried (MgSO$_4$) and concentrated by rotary evaporator. The crude product is purified using flash chromatography (7–14% EtOAc/hexanes). After evaporation of the appropriate fractions the product is further purified by treating a solution in Et$_2$O (100 mL) with charcoal, followed by filtration through Celite and evaporation. N-(2-chloro-5-cyclopropyl-6-fluorophenyl)-carbamic acid methyl ester is obtained as a white crystalline solid (m.p. 100–102° C.).

N-(2-chloro-5-cyclopropyl-6-fluorophenyl)-carbamic acid methyl ester (2.3 g, 9.4 mmol) is dissolved in MeOH (50 mL), water (50 mL) and 30% NaOH solution (50 mL). The reaction mixture is heated to reflux temperature for 3 days and then cooled to room temperature. The reaction is concentrated by rotary evaporator to remove most of the methanol and then partitioned between Et$_2$O (250 mL) and water (250 mL). The aqueous phase is extracted again with Et$_2$O (150 mL) and the combined organic layers washed with brine (250 mL), dried and concentrated by rotary evaporator. The crude product is purified by bulb-to-bulb distillation. 2-Chloro-5-cyclopropyl-6-fluorcaniline is isolated as a colorless oil (b.p. 120–135° C. at ~20 mm of Hg).

O. 2-Chloro-4-methyl-5-cyclopropyl-6-fluoroaniline

2-Chloro-5-cyclopropyl-6-fluoroaniline (9.4 g, 50.6 mmol) and N-bromosuccinimide (9.4 g, 52.8 mmol) are dissolved with stirring in 100 mL of anhydrous DMF. The reaction mixture is stirred overnight and then most of the DMF is removed by rotary evaporator under high vacuum. The residue is partitioned between 1:1 Et$_2$O/hexane (500 mL) and water (500 mL). The organic layer is washed with brine (3×250 mL), dried (MgSO$_4$) and concentrated by rotary evaporator. The crude material is purified using flash chromatography (7% CH$_2$Cl$_2$/hexanes) to give 2-chloro-4-bromo-5-cyclopropyl-6-fluoroaniline as a light orange oil.

2-Chloro-4-bromo-5-cyclopropyl-6-fluoroaniline (14.0 g, 53 mmol), trimethylboroxine (13.4 g of 50% solution in THF, 53 mmol), tetrakis(triphenylphosphine)palladium(0) (2.5 g, 2.2 mmol) and potassium carbonate (14.0 g, 101 mmol) are combined and stirred in 250 mL of a 4:1 DME/water solution. The mixture is degassed by repeated alternating application of vacuum and positive nitrogen pressure (10×). The mixture is heated to reflux temperature for 2 days and then cooled to room temperature. Most of the DME is removed by rotary evaporator and the residual mixture is partitioned between Et$_2$O (500 mL) and water (500 mL). The organic phase is washed with brine (3×250 mL), dried (MgSO$_4$) and concentrated by rotary evaporator. The crude product is purified using flash chromatography (5% CH$_2$Cl$_2$/hexanes) to give 2-chloro-4-methyl-5-cyclopropyl-6-fluoroaniline a light yellow oil.

P. 2-Fluoro-4-chloro-6-cyclopropylaniline

6-Bromo-4-chloro-2-fluoroaniline (2.0 g, 8.91 mmol), cyclopropylboronic acid (1.53 g, 17.8 mmol), K$_3$PO$_4$ (6.61 g, 31.2 mmol) and tricyclohexyl phosphine (0.249 g, 0.89 mmol) are dissolved in toluene (31 mL) and water (10 mL). The solution is degassed with N$_2$, heated to 90° C., and Pd(OAc)$_2$ (0.25 g, 1.16 mmol) is added. The reaction mixture is heated at 100° C. for 18 hours, cooled over 48 hours and loaded directly on a column of silica gel for purification by column chromatography (EtOAc/hexanes) to give 2-fluoro-4-chloro-6-cyclopropylaniline.

Q. 2-Chloro-4-cyclopropyl-5-methyl-3,6-difluoroaniline 1,4-Dibromo-2,5-difluorobenzene (100 g, 0.37 mol) is dissolved in concentrated sulfuric acid (200 g) and treated with fuming nitric acid (56 g, 0.44 mol, HNO$_3$ content >90%) by drop-wise addition at an internal temperature that is maintained between 50–60° C. After the addition is complete, the mixture is cooled to room temperature and stirred for 12 hours, then poured into ice-water (1000 mL). The suspension is extracted with EtOAc (3×500 mL). The combined organic extracts are dried (MgSO$_4$) and concentrated by rotary evaporator to give 2,5-dibromo-3,6-difluoronitrobenzene as an oily yellow solid.

2,5-Dibromo-3,6-difluoronitrobenzene (120 g, 0.37 mol) is dissolved in a mixture of ethanol (300 mL) and concentrated HCl (500 mL). The mixture is heated to 80° C. and treated with iron powder (100 g, 1.78 mol) by portion-wise addition over 2 hours. After stirring for an additional hour, the mixture is cooled to room temperature and EtOAc (800 mL) is added. The solids are removed by filtration and then the solution concentrated by rotary evaporator to remove most of the solvent. The residue is partitioned between EtOAc (1000 mL) and water (500 mL). The organic layer is washed with brine (2×250 mL), dried (MgSO$_4$) and concentrated by rotary evaporator to give a brown oil. The crude product is then purified using flash chromatography (9:1 hexanes/EtOAc) to give 2,5-dibromo-3,6-difluoroaniline.

2,5-Dibromo-3,6-difluoroaniline (50 g, 0.17 mol) is dissolved in glacial acetic acid (100 mL), stirred at room temperature, and treated with acetic anhydride (50 g, 0.49 mol). The reaction mixture becomes warm and is then allowed to cool to room temperature over the next 3 hours. The mixture is poured into EtOAc (500 mL) and extracted with water (2×300 mL), saturated sodium bicarbonate solution (2×300 mL) and then brine (2×300 mL). The solvent is removed by rotary evaporator and the residue triturated with a mixture of hexanes and Et$_2$O (2:1) to give 2,5-dibromo-3,6-difluoroacetanilide as a tan solid.

Copper(I) chloride (13.2 g, 0.13 mol) and Copper(II) chloride (18.0 g, 0.13 mol) are stirred in anhydrous DMF (150 mL) for 20 minutes. 2,5-Dibromo-3,6-difluoroacetanilide (44 g, 0.13 mol) is added and the mixture stirred at 80° C. for 4 hours, after which the temperature is increased to 100° C. for 16 hours. After cooling to room temperature most of the DMF is removed by rotary evaporator under high vacuum and the residue partitioned between EtOAc (500 mL) and water (500 mL). The organic layer is washed with brine (5×250 mL), dried (MgSO$_4$) and concentrated by rotary evaporator. The crude product is purified using flash chromatography (4:1, hexanes/EtOAc) to give 2-chloro-5-bromo-3,6-difluoroacetanilide as a white solid (m.p. 164–168° C.).

2-Chloro-5-bromo-3,6-difluoroacetanilide (10 g, 35 mmol), trimethylboroxine (8.8 g of 50% solution in THF, 35 mmol), tetrakis(triphenylphosphine)palladium(0) (0.8 g, 0.7 mmol) and potassium carbonate (8.6 g, 62 mmol) are combined and stirred in 120 mL of a 5:1 DME/water solution. The mixture is degassed by repeated alternating application of vacuum and positive nitrogen pressure (10×). The mixture is heated to reflux temperature for 2 days and then cooled to room temperature. Most of the DME is removed by rotary evaporator and the residual mixture is partitioned between EtOAc (250 mL) and water (250 mL). The organic phase is washed with brine (3×150 mL), dried ($MgSO_4$) and concentrated by rotary evaporator. The crude product is purified using flash chromatography (10% EtOAc/hexanes) to give 2-chloro-5-methyl-3,6-difluoroacetanilide as a white solid.

2-Chloro-5-methyl-3,6-difluoroacetanilide-(6.2 g, 28 mmol) is stirred in a mixture of EtOH (50 mL) and concentrated HCl (50 mL) and heated to reflux temperature for 12 hours. After cooling to room temperature most of the solvent is removed by rotary evaporator and the residue is treated with 1 N NaOH solution (500 mL) and extracted with $Et_2O$ (3×150 mL). The combined organic extracts are washed with brine (2×250 mL), dried ($MgSO_4$) and concentrated by rotary evaporator. The residue is purified using flash chromatography (9:1 hexanes/EtOAC) to give 2-chloro-5-methyl-3,6-difluoroaniline.

A solution of 2-chloro-5-methyl-3,6-difluoroaniline (5.0 g, 28 mmol) in anhydrous methanol (25 mL) is treated with elemental bromine (5.0 g, 3,1 mmol) at room temperature. After stirring for 12 hours, most of the solvent is removed by rotary evaporator and the residue partitioned between EtOAc (250 mL) and water (250 mL). The organic phase is washed with brine (150 mL), dried ($MgSO_4$) and concentrated by rotary evaporator. The crude product is purified using flash chromatography (7% EtOAc/hexanes) to give 2-chloro-4-bromo-5-methyl-3,6-difluoroaniline as a tan solid.

A mixture of 2-chloro-4-bromo-5-methyl-3,6-difluoroaniline (7.0 g, 27 mmol) cyclopropylboronic acid (3.5 g, 41 mmol), palladium(II) acetate (0.67 g, 3.0 mmol), potassium phosphate (17.5 g, 82 mmol) and tricyclohexylphosphine (0.83 g, 3.0 mmol) is dissolved in 100 mL of 4:1 toluene/water. The mixture is degassed by repeated alternating applications of vacuum and positive nitrogen pressure (10×). The mixture is heated to 95° C. for 2 days and then cooled to room temperature. Most of the toluene is removed by rotary evaporator and the residual mixture is partitioned between $Et_2O$ (250 mL) and water (250 mL). The organic phase is washed with brine (3×250 mL), dried ($MgSO_4$) and concentrated by rotary evaporator. The crude product is purified using flash chromatography (10% EtOAc/hexanes) to give 2-chloro-4-cyclopropyl-5-methyl-3,6-difluoroaniline as a tan oil.

R. 1-Chloro-3-fluoro-2-aminonaphthalene

To a solution of 3-amino-2-naphthoic acid (3.74 g, 20 mmol) and 48% fluoroboric acid (2.07 g, 30 mmol) in 10 mL of $H_2O$ cooled to 0° C. is added dropwise a solution of $NaNO_2$ (2.07 g, 30 mmol) in 15 mL of $H_2O$. The mixture is stirred at 0° C. for 1 hour. The mixture is filtered and the solids washed with cold $H_2O$, then MeOH, then $Et_2O$. The remaining solid is dried in vacuo at 40° C. for 2 days. The solid is suspended in xylene and heated to reflux for 8 hours and then cooled to room temperature. To the mixture is added hexane. The solid is filtered and washed with $CH_2Cl_2$, and dried to give 3-fluoro-2-naphthoic acid as a brown solid. A mixture of this solid and 80 mL of 1,4-dioxane is added to DPPA (4.5 mL, 20.9 mmol). Then 3.88 mL (27.9 mmol) of $Et_3N$ is added and the mixture is stirred for 2 hours at room temperature-under an atmosphere of nitrogen; Ethanol (8.1 mL, 139 mmol) is added, the mixture is heated to reflux for 2 hours, concentrated in vacuo and the residue diluted with 200 mL of EtOAc. The solution is washed with 5% aqueous $Na_2CO_3$ (50 mL), brine (50 mL), dried over $MgSO_4$ and evaporated to dryness to give a solid that is purified by flash chromatography on silica gel (100% $CH_2Cl_2$) to give N-(3-fluoro-2-naphthyl)carbamic acid ethyl ester.

To a solution of N-(3-fluoro-2-naphthyl)carbamic acid ethyl ester (0.91 g, 3.9 mmol) in 10 mL of HOAc heated to 50° C. is added dropwise 0.3 mL (3.9 mmol) of $SO_2Cl_2$. The mixture is stirred for 1.5 hours at 60° C. and then poured over 20 g ice. The mixture is extracted 4 times with 30 mL of $CH_2Cl_2$ and the combined organic layers are washed with saturated aqueous $NaHCO_3$ (50 mL), brine (50 mL), dried over $MgSO_4$ and evaporated to dryness to give N-(1-chloro-3-fluoro-2-naphthyl)carbamic acid ethyl ester as a brown solid. A mixture of this solid and 3.14 g (74.7 mmol) of $LiOH.H_2O$ in 30 mL of 30% EtOH/$H_2O$ is heated to reflux and stirred overnight. The solvents are evaporated in vacuo and the residue is extracted 3 times with 30 mL $CH_2Cl_2$. The combined organic layers are washed 3 times with 20 mL saturated aqueous brine, dried over $MgSO_4$ and evaporated to dryness to give 1-chloro-3-fluoro-2-aminomaphthalene as a brown solid.

S. 3-Chloro-2-aminonaphthalene

To a flask containing 35 mL of concentrated $H_2SO_4$ is added 3.31 g $NaNO_2$ (47.9 mmol) slowly over 15 minutes. The mixture is stirred an additional 15 minutes before being cooled to room temperature in a cold water bath. A solution of 8.14 g 3-amino-2-naphthoic acid (43.5 mmol) in 65 mL HOAc is added slowly dropwise, keeping the reaction temperature below 40° C. The mixture is stirred for 30 minutes and then poured carefully into an ice-cold solution of 10.14 g CuCl (102.2 mmol) in 65 mL of concentrated HCl. The mixture is heated to 80° C. and stirred for 30 minutes before adding 200 mL of $H_2O$. After stirring an additional 15 minutes, the mixture is filtered and washed with $H_2O$ to give a gray solid. The solid is dissolved in 500 mL of $CH_2Cl_2$ and the solution is washed 2 times with 100 mL saturated aqueous brine and dried over $Na_2SO_4$. Evaporation of the solvents gives a solid that is dried in vacuo to give 3-chloro-2-naphthoic acid as a brown solid.

To a solution of 1.70 g of 3-chloro-2-naphthoic acid (8.23 mmol) in 50 mL of 1,4-dioxane is added 2.3 mL of triethylamine (16.45 mmol) followed by 2.7 mL of DPPA (12.34 mmol). The mixture is stirred for 2 hours at room temperature under an atmosphere of nitrogen. Then 4.8 mL (82.3 mmol) of EtOH is added and the reaction is heated to reflux and stirred for an additional 2 hours. The solvents are evaporated in vacuo and the remaining residue is dissolved in 50 mL of EtOAc and washed with 20 mL of 5% aqueous citric acid, 20 mL of 5% $Na_2CO_3$ and dried over $MgSO_4$. The solvents are evaporated to give a residue that is purified by flash chromatography on silica gel (50% $CH_2Cl_2$/hexane) to give N-(3-chloro-2-naphthyl)carbamic acid ethyl ester as a yellow oil.

A mixture of 2.94 g (11.77 mmol) of N-(3-chloro-2-naphthyl)carbamic acid ethyl ester, and 7.93 g (141.2 mmol) KOH in 80 mL of EtOH is heated to reflux for 7 hours under an atmosphere of nitrogen. After cooling to room temperature, the solvent is evaporated in vacuo giving a residue to which ice is added. The mixture is extracted 3 times with 30 mL of $CH_2Cl_2$. The combined organic layers are dried over $Na_2SO_4$ and the solvents evaporated to give 3-chloro-2-aminonaphthalene as a brown solid.

T. 1,3-Dichloro-2-aminonaphthalene

To a solution of 0.48 g (2.7 mmol) of 3-chloro-2-aminonaphthalene in 2 mL of HOAc heated to 50° C. is added 0.8 mL (2.7 mmol) of $SO_2Cl_2$. The mixture is stirred at 60° C. for 1 hour and then poured over 15 g of ice. The mixture is adjusted to pH 4 with saturated aqueous $NaHCO_3$ and extracted 3 times with 20 mL of $CH_2Cl_2$. The combined organic layers are washed 2 times with saturated brine, dried over $MgSO_4$ and the solvents evaporated to give 1,3-dichloro-2-aminonaphthalene as a brown solid.

U. 1-Fluoro-2-aminonapthalene

A solution of 3.05 g (21.3 mmol) of 2-aminonaphthalene and 3.56 mL (25.6 mmol) of triethylamine in 100 mL of $CH_2Cl_2$ is cooled to 0° C., and 1.59 mL (22.4 mmol) of acetyl chloride is added dropwise. The reaction is allowed to warm to room temperature and is stirred under an atmosphere of nitrogen for 4 hours. The mixture is diluted with 100 mL of $CH_2Cl_2$ and washed with 50 mL each of 1 N HCl, $H_2O$, saturated aqueous $NaHCO_3$ and brine. The organic layer is dried over $MgSO_4$, filtered and the solvent evaporated to give 2-acetylaminonaphthalene as a brown solid.

A mixture of 1.95 g (10 mmol) of 2-acetylaminonaphthalene, and 7.1 g (20 mmol) of 1-(chloromethyl)-4-fluoro-1,4-diazoniabicyclo[2.2.2]octane bis(tetrafluoroborate) (Selectfluor®) in 30 mL of $CH_3CN$ is heated to reflux under an atmosphere of nitrogen for 24 hours. After cooling to room temperature, 50 mL of EtOAc is added and the mixture is washed with $H_2O$ and dried over $MgSO_4$. Evaporation of the solvents gives a syrup that is purified by flash chromatography on silica gel (25% EtOAc/hexane) to give 1-fluoro-2-acetylaminonaphthalene.

A mixture of 1.31 g (6.43 mmol) of 1-fluoro-2-acetylaminonaphthalene in 15 mL of 6 N HCl and 15 mL of EtOH under a nitrogen atmosphere is heated to reflux for 3 hours and then allowed to cool to room temperature. The reaction is neutralized with saturated aqueous $NaHCO_3$ and extracted 3 times with 30 mL of $CH_2Cl_2$. The combined organic layers are washed 2 times with 20 mL saturated brine, dried over $MgSO_4$ and the solvents evaporated to give 1-fluoro-2-aminonaphthalene.

V. 1-Fluoro-3-chloro-2-aminonaphthalene

A mixture of 2.50 g (10 mmol) of N-(3-chloro-2-naphthyl)carbamic acid ethyl ester and 7.1 g of Selectfluor® (20 mmol) in 30 mL of $CH_3CN$ is heated to reflux under an atmosphere of nitrogen for 16 hours. After cooling to room temperature, the solids are filtered and the solvent is evaporated to give a residue that is diluted with 200 mL of EtOAc. The mixture is washed 3 times with 50 mL of $H_2O$, once with 50 mL of saturated brine and dried over $MgSO_4$. Evaporation of the solvents gives a residue that is purified by flash chromatography on silica gel (100% $CH_2Cl_2$) to give N-(1-fluoro-3-chloro-2-naphthyl)carbamic acid ethyl ester.

A mixture of 1.43 g (5.34 mmol) of N-(1-fluoro-3-chloro-2-naphthyl)carbamic acid ethyl ester, and 4.48 g (106.8 mmol) $LiOH.H_2O$ in 30 mL of EtOH and 70 mL of $H_2O$ is heated to reflux for 16 hours under an atmosphere of nitrogen. After cooling to room temperature, the mixture is concentrated in vacuo to give a residue that is extracted 3 times with 30 mL $CH_2Cl_2$. The combined organic layers are washed with 30 mL of saturated aqueous $NaHCO_3$, 30 mL of saturated brine, dried over $MgSO_4$ and the solvents evaporated to give 1-fluoro-3-chloro-2-aminonaphthalene as a brown solid.

W. 1,3-Difluoro-2-aminonaphthalene

A mixture of 1.63 g (7 mmol) of N-(3-fluoro-2-naphthyl)carbamic acid ethyl ester, and 2.73 g of Selectfluor® (7.7 mmol) in 10 mL of trifluoroacetic acid is heated to 70° C. under an atmosphere of nitrogen for 4 hours. After cooling to room temperature, the mixture is concentrated in vacuo and 30 mL of ice water is added. The mixture is extracted 3 times with 40 mL of $CH_2Cl_2$. The combined organic layers are washed with 40 mL each of $H_2O$, saturated aqueous $NaHCO_3$, saturated brine, dried over $MgSO_4$. Evaporation of the solvents gives a residue that is purified by flash chromatography on silica gel (50% $CH_2Cl_2$/hexane) to give N-(1,3-difluoro-2-naphthyl)carbamic acid ethyl ester, which is hydrolyzed to 1,3-difluoro-2-aminonaphthalene under conditions described above.

X. 1-Chloro-7-trifluoromethyl-2-aminonaphthalene

To a solution of 2,7-dinitronaphthalene (500 mg, 2.29 mmol) in methanol (5 mL) heated to reflux, is added over 15 minutes, a solution of sodium hydrosulfide (196 mg, 3.44 mmol) in methanol (5 mL) and water (10 mL). The reaction mixture is heated at reflux for 30 minutes and then poured into ice-water and filtered to give an orange solid. After washing the solid with boiling 10% aqueous HCl, the filtrate is basified with solid NaOH and extracted with EtOAc. The organic layer is dried ($Na_2SO_4$) and the solvents are evaporated to give 7-nitro-2-aminonaphthalene as a bright orange solid.

A suspension of 7-nitro-2-aminonaphthalene (260 mg, 1.38 mmol) in concentrated HCl (10 mL) is cooled to 0° C. Sodium nitrite (105 mg, 1.53 mmol) is added in portions and the reaction is allowed to stir at 0° C. for 30 minutes. A solution of iodide (175 mg, 253.8 mmol) and potassium iodide (459 mg, 2.76 mmol) in water (5 mL) is added dropwise. After stirring at 0° C. for 1 hour, the solid is removed by filtration. The solid is dissolved in EtOAc and washed with sodium metabisulfite solution, water and brine. The organic layer is dried ($Na_2SO_4$) and the solvents evaporated to give 2-iodo-7-nitronaphthalene as an orange solid.

A mixture of 2-iodo-7-nitronaphthalene (1 g, 3.34 mmol), trifluoromethyliodide (0.328 mL, 4.01 mmol) and copper powder (2.55 g, 40.1 mmol) in pyridine (20 mL) in a sealed tube is heated with stirring at 120° C. for 20 hours. After cooling, the reaction mixture is filtered and extracted with EtOAc. The organic extracts are washed with water, 0.1 M citric acid solution and dried ($Na_2SO_4$). Concentration and purification of the residual oil by flash chromatography on silica gel (2:1 hexanes/EtOAc) gives 2-nitro-7-trifluoromethylnaphthalene as a yellow solid.

A mixture of 2-nitro-7-trifluoromethylnaphthalene (650 mg, 2.7 mmol) and Raney nickel (65 mg) in methanol (10 mL) is stirred under $H_2$ (1 atm) for 1 hour. Filtration of the catalyst and evaporation of the solvent gives 7-trifluoromethyl-2-aminonaphthalene as a yellow solid.

To a solution of 7-trifluoromethyl-2-aminonaphthalene (550 mg, 2.60 mmol) and triethylamine (1.09 mL, 7.81 mmol) in dichloromethane (10 mL) at room temperature is added acetyl chloride (0.222 mL, 3.13 mmol) dropwise. After stirring at room temperature for 1.5 hours, the mixture is partitioned between dichloromethane and water. The organic layer is washed with 0.1 M citric acid solution, brine, dried (MgSO$_4$) and concentrated by rotary evaporator to give 7-trifluoromethyl-2-acetamidonaphthalene as a light yellow solid.

A mixture of 7-trifluoromethyl-2-acetamidonaphthalene (620 mg, 2.45 mmol), N-chlorosuccinimide (326 mg, 2.45 mmol) and 1 M HCl in acetic acid (2.45 mL, 2.45 mmol) in acetic acid (10 mL) is heated at 50° C. under a N$_2$ atmosphere for 1 hour. After cooling to room temperature, the mixture is partitioned between EtOAc and water. The organic layer is washed with brine, dried (Na$_2$SO$_4$) and concentrated by rotary evaporator to give 1-chloro-7-trifluoromethyl-2-acetamidonaphthalene as an off-white solid.

A mixture of 1-chloro-7-trifluoromethyl-2-acetamidonaphthalene (700 mg, 2.43 mmol), water (3 mL) and concentrated sulfuric acid (3 mL in ethanol (6 mL) is heated to reflux temperature under a N$_2$ atmosphere for 1 hour. After cooling to room temperature, the mixture is extracted with EtOAc. The extracts are washed with water, brine, dried (Na$_2$SO$_4$) and concentrated. Flash chromatography on silica gel (3:1 hexanes/EtOAc) gives 1-chloro-7-trifluoromethyl-2-aminonaphthalene as a white solid.

Y. 1-Chloro-6-methoxy-2-aminonaphthalene

To a suspension of 6-hydroxy-2-naphthoic acid (5 g, 26.6 mmol) and triethylamine (7.39 mL, 53.1 mmol) in 1,4-dioxane (50 mL) at room temperature, is added DPPA (8.59 mL, 39.9 mmol). After stirring at room temperature for 2.5 hours, ethanol (15.5 mL, 266 mmol) is added and the reaction is heated to reflux temperature overnight. After cooling to room temperature, the mixture is partitioned between EtOAc and water. The organic layer is washed with brine, dried (Na$_2$SO$_4$) and concentrated by rotary evaporator to give an oil. Flash chromatography on silica gel (5% methanol in dichloromethane) gives N-(6-hydroxy-2-naphthyl)carbamic acid ethyl ester as a white solid.

To a solution of N-(6-hydroxy-2-naphthyl)carbamic acid ethyl ester (1 g, 4.32 mmol) and triethylamine (1.80 mL, 13 mmol) in dichloromethane (20 mL) at room temperature, is added acetyl chloride (0.369 mL, 5.19 mmol) dropwise. After stirring at room temperature for 3 hours, the reaction mixture is concentrated and purified by flash chromatography on silica gel (2:1 hexane/EtOAc) to give N-(6-acetyloxy-2-naphthyl)carbamic acid ethyl ester as a white solid.

A mixture of N-(6-acetyloxy-2-naphthyl)carbamic acid ethyl ester (670 mg, 2.45 mmol), N-chlorosuccinimide (326 mg, 2.45 mmol) and 1 M HCl in acetic acid (2.45 mL, 2.45 mmol) in acetic acid (10 mL) is heated at 50° C. under N$_2$ atmosphere for 1 hour. After cooling to room temperature the mixture is partitioned between EtOAc and water. The organic layer is washed with brine, dried (Na$_2$SO$_4$) and concentrated by rotary evaporator to give N-(6-acetyloxy-1-chloro-2-naphthyl)carbamic acid ethyl ester as a white solid.

A mixture of N-(6-acetyloxy-1-chloro-2-naphthyl)carbamic acid ethyl ester (375 mg, 1.34 mmol) and KOH (903 mg, 16.1 mmol) in ethanol (10 mL) is heated to reflux temperature under N$_2$ atmosphere for 4.5 hours. The reaction mixture is concentrated by rotary evaporator under high vacuum. The residual oil is partitioned between EtOAc and water. After acidification (2 N HCl), the organic layer is separated, washed with brine and dried (MgSO$_4$). Concentration by rotary evaporator gives 1-chloro-2-amino-6-naphthol as a brown solid.

A mixture of 1-chloro-2-amino-6-naphthol (250 mg, 1.29 mmol), benzaldehyde (0.144 mL, 1.42 mmol) and Na$_2$SO$_4$ in THF (10 mL) is heated to reflux temperature overnight. After cooling to room temperature, the reaction mixture is filtered, washed with EtOAc and concentrated by rotary evaporator to give a brown residue, which is used directly in the next step.

A mixture of the above residue (360 mg, 1.28 mmol), NaOH (102 mg, 2.56 mmol) and methyl iodide (0.159 mL, 2.56 mmol) in acetone (10 mL) is stirred at room temperature for 2 hours. After concentration, the obtained crude product is used in the next step.

A solution of the above crude product (378 mg, 1.28 mmol) in THF (10 mL) is treated with 2 N HCl (20 mL). After stirring at room temperature overnight, the reaction mixture is partitioned between EtOAc and water. The organic layer is washed with brine, dried (Na$_2$SO$_4$) and concentrated by rotary evaporator. The residual oil is purified by flash chromatography on silica gel (2:1 hexanes/EtOAc) to give 1-chloro-6-methoxy-2-aminonaphthalene.

Z. 1-Chloro-6-fluoro-2-aminonaphthalene

To a solution of 6-amino-2-naphthoic acid (1 g, 5.34 mmol) in ethanol (20 mL), is added dropwise thionyl chloride (0.622 mL, 10.7 mmol). The resulting reaction solution is heated to reflux temperature under a N$_2$ atmosphere for 3 hours. Concentration and trituration with methanol gives 6-amino-2-naphthoic acid ethyl ester as a brown oil.

A mixture of 6-amino-2-naphthoic acid ethyl ester (500 mg, 2.32 mmol) and nitrosonium tetrafluoroborate (298 mg, 2.56 mmol) in 1,2-dichlorobenzene (10 mL) is stirred at room temperature for 12 hours and at 110° C. for 1 hour. After cooling to room temperature, the reaction mixture is concentrated by rotary evaporator under high vacuum. The residual oil is purified by flash chromatography on silica gel (dichloromethane) to give 6-fluoro-2-naphthoic acid ethyl ester as a yellow oil.

To a solution of 6-fluoro-2-naphthoic acid ethyl ester (600 mg, 2.75 mmol) in ethanol (10 mL) at room temperature, is added 1 N NaOH (2.75 mL, 2.75 mmol). After stirring at room temperature for 4 hours, water (10 mL) is added. Acidification (2 N HCl) and filtration gives 6-fluoro-2-naphthoic acid as a white solid.

To a suspension of 6-fluoro-2-naphthoic acid (450 mg, 2.37 mmol) and triethylamine (0.66 mL, 4.73 mmol) in 1,4-dioxane (30 mL) at room temperature, is added DPPA (0.77 mL, 3.55 mmol). After stirring at room temperature for 2.5 hours, ethanol (1.38 mL, 23.7 mmol) is added and the reaction is heated to reflux temperature for 12 hours. After cooling to room temperature, the mixture is partitioned between EtOAc and water. The organic layer is washed with brine, dried (Na$_2$SO$_4$) and concentrated by rotary evaporator to give an oil. Flash chromatography on silica gel (3:1 hexanes/EtOAc) gives N-(6-fluoro-2-naphthyl)carbamic acid ethyl ester as an oil.

A mixture of N-(6-fluoro-2-naphthyl)carbamic acid ethyl ester (548 mg, 2.35 mmol), N-chlorosuccinimide (313 mg, 2.35 mmol) and 1 M HCl in acetic acid (2.35 mL, 2.35 mmol) in acetic acid (20 mL) is heated at 50° C. under N$_2$ atmosphere for 1 hour. After cooling to room temperature, water (10 mL) is added. The resulting precipitate is removed by filtration to give N-(1-chloro-6-fluoro-2-naphthyl)carbamic acid ethyl ester as a yellow solid.

A mixture of N-(1-chloro-6-fluoro-2-naphthyl)carbamic acid ethyl ester (600 mg, 2.24 mmol) and KOH (1.51 g, 26.9 mmol) in ethanol (20 mL) is heated to reflux temperature under N$_2$ atmosphere for 12 hours. After cooling, the reaction mixture is concentrated by rotary evaporator. The residual oil is purified by flash chromatography on silica gel (3:1 hexanes/EtOAc) to give 1-chloro-6-fluoro-2-aminonaphthalene as a brown solid.

AA. 1,6-Dichloro-2-aminonaphthalene

Sodium nitrite (811 mg, 11.8 mmol) is added over a period of 15 minutes to concentrated sulfuric acid (10 mL) while stirring. The mixture is heated to 70° C. for 15 minutes. After cooling to room temperature, a solution of 6-amino-2-naphthoic acid (2 g, 10.7 mmol) in acetic acid (10 mL) is added dropwise at such a rate that the temperature is kept below 40° C. After stirring at 40° C. for an additional 30 minutes, the reaction mixture is poured into an ice-cooled solution of copper(I) chloride (2.54 g, 25.6 mmol) in concentrated HCl (30 mL). After stirring at 80° C. for 30 minutes, water (80 mL) is added. The precipitate is collected and purified by flash chromatography on silica gel (5% methanol in dichloromethane) to give 6-chloro-2-naphthoic acid as a brown solid.

To a suspension of 6-chloro-2-naphthoic acid (1 g, 4.84 mmol) and triethylamine (1.35 mL, 9.68 mmol) in 1,4-dioxane (20 mL) at room temperature, is added DPPA (1.56 mL, 7.26 mmol). After stirring at room temperature for 2.5 hours, ethanol (2.82 mL, 48.4 mmol) is added and the reaction is heated to reflux temperature for 12 hours. After cooling to room temperature, the mixture is partitioned between EtOAc and water. The organic layer is washed with brine, dried ($Na_2SO_4$) and concentrated by rotary evaporator to give an oil. Flash chromatography on silica gel (3:1 hexanes/EtOAc) gives N-(6-chloro-2-naphthyl)carbamic acid ethyl ester as a white solid.

A mixture of N-(6-chloro-2-naphthyl)carbamic acid ethyl ester (725 mg, 2.90 mmol), N-chlorosuccinimide (387 mg, 2.90 mmol) and 1 M HCl in acetic acid (2.90 mL, 2.90 mmol) in acetic acid (20 mL) is heated at 50° C. under $N_2$ atmosphere for 1 hour. After cooling to room temperature, water (10 mL) is added and extracted with EtOAc. The organic layer is washed with brine, dried ($Na_2SO_4$) and concentrated by rotary evaporator to give N-(1,6-dichloro-2-naphthyl)carbamic acid ethyl ester as a yellow solid.

A mixture of N-(1,6-dichloro-2-naphthyl)carbamic acid ethyl ester (750 mg, 2.64 mmol) and KOH (1.78 mg, 31.7 mmol) in ethanol (20 mL) is heated to reflux temperature under a $N_2$ atmosphere for 12 hours. After cooling to room temperature, water (10 mL) is added. The resulting precipitation is removed by filtration to give 1,6-dichloro-2-aminonaphthalene as a solid.

BB. 1-Chloro-7-fluoro-2-aminonaphthalene

A mixture 7-nitro-2-aminonaphthalene (1 g, 5.31 mmol) and nitrosonium tetrafluoroborate (931 mg, 7.97 mmol) in dichloromethane (10 mL) is stirred at room temperature for 12 hours and at 110° C. for 1 hour. After cooling to room temperature, the reaction mixture is concentrated by rotary evaporator under high vacuum. The residual oil is purified by flash chromatography on silica gel (3:1 hexanes/EtOAc) to give 7-fluoro-2-nitronaphthalene as a dark red solid.

7-Fluoro-2-nitronaphthalene is converted to 1-chloro-7-fluoro-2-aminonaphthalene similarly to steps described for the preparation of 1-chloro-7-trifluoromethyl-2-aminonaphthalene.

CC. 4-Aminoquinolines (a) 4-Amino-7-chloro-2-trifluoromethylquinoline

A mixture of 7-chloro-2-trifluoromethyl-4-quinolinol (4 g, 16.2 mmol) in phosphorus oxychloride (7.55 mL, 81 mmol) is heated at reflux temperature for 3 hours. After cooling to room temperature, ice (200 g) is added, the mixture is neutralized with $NaHCO_3$ and extracted with EtOAc. The organic layer is washed with brine, dried ($Na_2SO_4$) and concentrated by rotary evaporator. The resulting tan residue is purified by flash chromatography on silica gel (1% ether in hexanes) to give 4,7-dichloro-2-trifluoromethylquinoline as a solid.

A solution of 4,7-dichloro-2-trifluoromethylquinoline (2 g, 7.52 mmol) in dioxane (10 mL) and $NH_3$ (2 mL) are mixed at −78° C. in a sealed tube. After sealing and warming up to room temperature, the reaction is heated at 60–70° C. for 19 hours and at 120° C. for 3 hours. The sealed tube is cooled to −78° C. before it is opened and the contents are concentrated by rotary evaporator. 4-Amino-7-chloro-2-trifluoromethylquinoline is obtained as a solid by trituration of the residue with ether.

(b) 4-Amino-2,7-bis(trifluoromethyl)quinoline

4-Amino-2,7-bis(trifluoromethyl)quinoline is similarly prepared from 4-chloro-2,7-bis(trifluoromethyl)quinoline using ammonia in methanol and is purified by flash chromatography on silica gel (10% EtOAc in hexanes).

(c) 4-Amino-7-fluoroquinoline

4-Amino-7-fluoroquinoline is similarly prepared from 4-chloro-7-fluoroquinoline.

(d) 4-Amino-6-fluoro-2-(trifluoromethyl)quinoline

A mixture of 4-chloro-6-fluoro-2-(trifluoromethyl)quinoline (1 g, 4.01 mmol) and $NH_3$ (3 mL) in ethylene glycol (20 mL) is prepared at −78° C. in a sealed tube. After warming up to room temperature, the sealed tube is gradually heated to 100° C. overnight. After cooling to −78° C., the sealed tube is opened and the contents are concentrated by rotary evaporator. The residue is purified by flash chromatography on silica gel (1:3 EtOAc/hexanes) to give 4-amino-6-fluoro-2-(trifluoromethyl)quinoline as a light yellow solid.

Example 2

2-(Iodo or Bromo)-Phenylacetic Acid Ester and Phenylacetamide Starting Materials A. Prepared According to, e.g., *J Med Chem*, Vol. 33, pp. 2358–2368 (1990), U.S. Pat. No. 6,291,523 and International Application WO 99/11605, Starting from the Corresponding Benzoic Acid or 2-indolinone, are:

N,N-dimethyl-5-methyl-2-iodophenylacetamide;
N,N-dimethyl-5-ethyl-2-iodophenylacetamide;
N,N-dimethyl-2-iodophenylacetamide;
N,N-dimethyl-5-chloro-2-iodophenylacetamide; and
N,N-dimethyl-5-fluoro-2-iodophenylacetamide.

B. N,N-Dimethyl-2-bromo-5-cyclopropylphenylacetamide

Methyl iodide (13 g, 91.5 mmol) is added to slurry of 2-bromo-5-iodobenzoic acid (23 g, 70.4 mmol) and $K_2CO_3$ (14.6 g, 106 mmol) in DMF (50 mL) at room temperature. After TLC shows complete consumption of the starting material, the reaction is diluted with $Et_2O$ and washed three times with a saturated aqueous solution of NaCl. The combined aqueous layers are extracted once with fresh $Et_2O$ and once with EtOAc. The organic layers are combined, dried with $Na_2SO_4$, filtered and concentrated to an oil. The oil is diluted with a minimal amount of $Et_2O$ and filtered through a plug of silica. The silica is rinsed with a 20% ether/hexanes mixture. The eluents are concentrated in vacuo to give 2-bromo-5-iodobenzoic acid methyl ester as a solid.

The reaction of the above iodide with cyclopropyl bromide and InCl₃ according to method outlined in *J. Am. Chem. Soc.* (2001), supra, yields 2-bromo-5-cyclopropylbenzoic acid methyl ester as a solid.

To a solution of 2-bromo-5-cyclopropylbenzoic acid methyl ester (1.82 g) in THF (31 mL) is added 9 mL of a 1.0 M solution of LAH in THF by syringe. After 2 hours at room temperature, the reaction is quenched with 2 N NaOH and partitioned between ethyl acetate and water. The organic phase is separated, washed with brine, dried (Na₂SO₄) and concentrated in vacuo to give the corresponding benzyl alcohol as a solid.

To a solution of the above benzyl alcohol (28 g) in ether (600 mL) is added PBr₃. (23 mL) by pipette and the reaction is stirred overnight at room temperature. The reaction is quenched by the slow addition of cold H₂O. The organic phase is washed with brine, dried (Na₂SO₄) and concentrated in vacuo to afford the benzyl bromide as a yellow oil.

To a solution of the above benzyl bromide (13.2 g) in DMF (150 mL) is added a solution of KCN (5.85 g) in water (50 mL). The reaction is heated at 50° C. for 90 minutes, cooled and partitioned between EtOAc and water. The EtOAc layer is separated, washed 3× with brine, dried over Na₂SO₄ and concentrated in vacuo to afford 2-bromo-5-cyclopropylphenylacetonitrile as a light yellow oil.

To a solution of the above nitrile (12 g) in EtOH (400 mL), is added NaOH (36.6 g) and water (200 mL). The reaction is refluxed for 2 hours and cooled to room temperature. After the ethanol is removed under reduced pressure, the residue is cooled to 0° C. and acidified to pH 1–2 with 3 N HCl. The phenylacetic acid is extracted into ethyl acetate and the aqueous layer discarded. The organic phase is washed with brine, dried (Na₂SO₄) and concentrated in vacuo to afford 2-bromo-5-cyclopropylphenylacetic acid.

The above acid (23.1 g) is dissolved in CH₂Cl₂. N₁N-Dimethylamine hydrochloride (7.75 g), 182 mL of a 0.5 M solution of HOAt in DMF, NMM (60 mL) and EDCI (35 g) are added. The reaction is allowed to stir overnight, washed with a sodium bicarbonate solution and brine, and dried with Na₂SO₄. The methylene chloride is removed under reduced pressure and the residue is diluted with ether before filtering through a plug of silica gel. Removal of the ether in vacuo yields N,N-dimethyl-2-bromo-5-cyclopropylphenylacetamide.

C. N,N-Dimethyl-5-bromo-2-iodophenylacetamide

5-Bromo-2-iodobenzoic acid (100 g, 0.306 mol) is dissolved in THF (350 mL) and cooled in an ice bath. Borane-THF complex (460 mL of 1 M in THF, 0.460 mol) is added dropwise. After addition is complete, the reaction is warmed to room temp and stirred for 14 hours. The mixture is transferred a large erlenmeyer flask (4 L), cooled in an ice bath and carefully quenched with water (250 mL). Evaporation of the THF by rotary evaporator gives a white suspension which is treated with additional water (1 L) and then filtered and dried in a vacuum dessicator over P₂O₅ to give 5-bromo-2-iodobenzyl alcohol.

The above benzyl alcohol is dissolved in 48% HBr (500 mL and heated at reflux temperature for 4 hours. The resulting benzyl bromide is isolated as a yellow solid by pouring the cooled mixture into a large volume (1.5 L) of water followed by filtration. The benzyl bromide is dissolved in EtOH (400 mL) and stirred at room temperature. Sodium cyanide (56 g, 1.14 mol) is dissolved in a minimum amount (~100 mL) of water and then added to the ethanolic solution of the benzyl bromide. The reaction is heated to reflux temperature for 3 hours and then cooled to room temperature. Ethanol is removed by rotary evaporator and the residue washed with a large volume (1 L) of water. The resulting 5-bromo-2-iodophenylcetonitrile is isolated by filtration.

The above phenylacetonitrile is dissolved in EtOH (350 mL) and treated with NaOH (32 g, 0.8 mol) which had been dissolved in water (200 mL). The reaction is heated at reflux temperature for 14 hours. After cooling to room temperature, ethanol is removed by rotary evaporator and 6 N HCl added until the pH=1. The solid 5-bromo-2-iodophenylacetic acid that formed is filtered and washed with water (2×500 mL). After drying over P₂O₅ in a vacuum dessicator, 5-bromo-2-iodophenylacetic acid (m.p. 165–169° C.) (102 g, 0.3 mol) is dissolved in CH₂Cl₂ (450 mL) that contains several drops of DMF. Thionyl chloride (32 mL, 0.450 mol) is added and the reaction heated to reflux temperature overnight. After cooling to room temperature, the reaction mixture is diluted with additional CH₂Cl₂ (500 mL) and washed with water (2×250 mL), saturated NaHCO₃ (250 mL) and brine (250 mL). The solution is dried (MgSO₄) and concentrated by rotary evaporator to give 5-bromo-2-iodophenylactetyl chloride as a yellowish oil.

Dimethylamine (200 mL of 2 M in THF) is added dropwise to a solution of the above 5-bromo-2-iodophenylacetyl chloride in Et₂O (500 mL), cooled in an ice bath. After the addition is complete, EtOAc (350 mL) is added and the solution washed with water (350 mL), brine (250 mL) and dried (MgSO₄). Evaporation by rotary evaporator and trituration with 1:1 Et₂O/hexanes gives N,N-dimethyl-5-bromo-2-iodophenylacetamide (m.p. 127–129° C.).

D. N,N-Dimethyl-5-methoxy-2-bromophenylacetamide

5-Methoxy-2-bromobenzoic acid (85 g, 0.37 mol) is dissolved in anhydrous THF (100 mL) and cooled in an ice-salt bath until the temperature reaches −5° C. Borane-THF complex is added dropwise as a 1.0 M solution in THF (736 mL, 0.74 mol) at −5° C. After addition is complete, the reaction mixture is slowly warmed to room temperature and stirred for 12 hours. Water (40 mL) is slowly added dropwise and the reaction mixture stirred for 30 minutes. Additional water (350 mL) is added and the mixture is concentrated by rotary evaporator to remove most of the THF. The remaining material is extracted with EtOAc (800 mL). The organic layer is washed with saturated NaHCO₃ (500 mL), brine (250 mL) and then dried (Na₂SO₄). Upon removal of the solvent by rotary evaporator, 5-methoxy-2-bromobenzyl alcohol is obtained as a white solid.

5-Methoxy-2-bromobenzyl alcohol (79.5 g, 0.37 mol) is dissolved in 48% HBr (400 mL) and heated to reflux temperature for 4 hours. The reaction mixture is cooled to room temperature and poured into water (1500 mL). The solution is extracted with EtOAc (2×500 mL). The combined organic layers are dried (MgSO₄) and concentrated by rotary evaporator. The crude material is then purified using flash chromatography (CH₂Cl₂/hexanes, from 1:1 to 4:1) to give 5-methoxy-2-bromobenzyl bromide.

5-Methoxy-2-bromobenzyl bromide (72.8 g, 0.26 mol) is dissolved in EtOH (280 mL) and stirred at room temperature. Sodium cyanide (38.2 g, 0.78 mol) is dissolved in water and added to the solution of the bromide. The reaction mixture is heated to reflux temperature for 3 hours and then cooled to room temperature. Most of the ethanol is removed by rotary evaporator. A solid forms which is isolated by filtration and washed with water (500 mL). The crude material is purified using flash chromatography (CH₂Cl₂/hexanes, 1:1) to give 5-methoxy-2-bromophenylacetonitrile (53 g).

5-Methoxy-2-bromophenylacetonitrile (52.8 g, 0.23 mol) is dissolved in ethanol (250 mL) and stirred at room temperature. Sodium hydroxide (9.3 g, 0.47 mol) is dissolved in water (150 mL) and added to the solution of the nitrile. The mixture is heated to reflux temperature for 12 hours and then cooled to room temperature. Most of the ethanol is removed using a rotary evaporator and the residual aqueous solution adjusted to pH 4 with 3 N HCl. The solid which forms is isolated by filtration and washed with water. Air drying gives 5-methoxy-2-bromophenylacetic acid.

5-Methoxy-2-bromophenylacetic acid (56 g, 0.23 mol) is dissolved in $CH_2Cl_2$ (350 mL) and a catalytic amount of DMF is added and the solution stirred and cooled to 0° C. Thionyl chloride (41 mL, 0.34 mol) is added dropwise. The reaction mixture is heated at reflux temperature overnight and then cooled to room temperature. Solvents are removed by rotary evaporator. Twice benzene (500 mL) is added to the residual oil and the benzene solution is evaporated by rotary evaporator to remove any additional volatile components. The residual oil is crystallized from hexanes to give 5-methoxy-2-bromophenylacetyl chloride.

5-Methoxy-2-bromophenylacetyl chloride (60 g, 0.23 mol) is dissolved in anhydrous $Et_2O$ (400 mL), stirred and cooled in an ice bath. A 2 M solution of dimethylamine (228 mL, 0.46 mol) is added dropwise and the mixture allowed to warm to room temperature and stirred for 2 hours. Additional $Et_2O$ (500 mL) is added. The organic solution is washed with 1 N HCl (2×500 mL), saturated $NaHCO_3$ (500 mL) and brine (500 mL). The organic layer is dried ($Na_2SO_4$) and concentrated by rotary evaporator. The residue is purified using flash chromatography (hexanes/EtOAc, from 7:3 to 1:9). Trituration of the crude product with $Et_2O$/hexanes gives N,N-dimethyl-5-methoxy-2-bromophenylacetamide as a white crystalline solid (m.p. 88–90° C.).

E. N,N-Dimethyl-2-iodo-5-trifluoromethoxyphenylacetamide

4-Trifluoromethoxyaniline (100 g, 0.58 mol), di-tert-butyl carbonate (127 g, 0.58 mol) and 1 N NaOH solution (250 mL) are dissolved in THF (200 mL) and stirred at room temperature for 12 hours. The reaction mixture is extracted with EtOAc (500 mL). The organic layer is washed with 1 N HCl (500 mL), brine (250 mL) and dried ($MgSO_4$). The solvent is removed by rotary evaporator to give N-BOC-4-trifluoromethoxyaniline.

The above BOC-protected aniline (144 g, 0.52 mol) is dissolved in anhydrous THF (800 mL), cooled in a dry-ice/EtOH bath and stirred. t-Butyllithium (672 mL of 1.7 M solution in hexanes) is slowly added dropwise. The reaction mixture is warmed to −30° C. for 3 hours to form the aryllithium. Solid $CO_2$ (excess, about 100 g) is added to the reaction mixture and stirring is continued at −30° C. for an additional 2 hours. The reaction is quenched by first addition of saturated ammonium chloride (250 mL) and then 1 N HCl solution (500 mL). The mixture is extracted with EtOAc (2×500 mL). The combined organic layers are washed with brine, dried ($MgSO_4$) and concentrated using a rotary evaporator. The residue is triturated with hexanes to give 2-(BOC-amino)-5-trifluoromethoxybenzoic acid as a white solid that is isolated by filtration.

The above benzoic acid (120 g, 0.37 mol) is suspended in 1,4-dioxane (200 mL), stirred and warmed to 80° C. until dissolved. The solution is allowed to cool to room temperature and hydrogen chloride is bubbled into the reaction mixture for 30 minutes. Stirring is continued for 2 hours, during which time a precipitate forms. The precipitate is collected and washed with ice-cold water (1000 mL) and $Et_2O$ (500 mL) to give 5-trifluoromethoxyanthranilic acid as a solid.

The above 5-trifluoromethoxyanthranilic acid (68.8 g, 0.31 mol) is suspended in a mixture of concentrated HCl (50 mL) and water (300 mL), cooled to 0° C. and stirred. Sodium nitrite (24.2 g 0.35 mol) dissolved in water (50 mL) is slowly added taking care to maintain the temperature of the reaction mixture below 5° C. Stirring is continued at 0° C. for 30 minutes. Potassium iodide (91 g, 0.55 mol) is dissolved in a mixture of concentrated $H_2SO_4$ (19 mL) and water (130 mL) and added dropwise to the reaction mixture while keeping the temperature of the reaction mixture below 10° C. The mixture is then heated to 100° C. and stirred for 2 hours. After cooling to room temperature, the mixture is partitioned between EtOAc (1000 mL) and saturated sodium bisulfite solution (500 mL). The organic layer is washed again with saturated sodium bisulfite solution (500 mL) and then brine (500 mL), dried ($MgSO_4$) and concentrated by rotary evaporator to give 5-trifluoromethoxy-2-iodobenzoic acid.

The 5-trifluoromethoxy-2-iodobenzoic acid is converted to N,N-dimethyl-2-iodo-5-trifluoromethoxyphenylacetamide similarly to previously described procedures.

F. Isopropyl 5-trifluoromethyl-2-iodophenylacetate

A mixture of 4-aminobenzotrifluoride (100 g, 0.62 mol) and di-tert-butyl carbonate (150 g, 0.69 mol) in anhydrous THF (400 mL) is heated at reflux temperature for 6 hours and then cooled to room temperature. Most of the solvent is removed using a rotary evaporator and the non-volatile material that remains is triturated with water (1000 mL) to form a solid. The solid is isolated by filtration and washed with additional water (500 mL), then washed with hexanes (500 mL) to give 4-(BOC-amino)benzotrifluoride (m.p. 123–124° C.).

4-(BOC-amino)benzotrifluoride (143 g, 0.55 mol) is dissolved in anhydrous THF (800 mL) and cooled in a dry-ice/ethanol bath. A solution of tert-butyllithium (709 mL of 1.7 M) in pentane is then slowly added via a dropping funnel. After the addition is complete, the reaction mixture is allowed to warm to −30° C. and stirred, at that temperature, for 2 hours. The reaction mixture is cooled to −78° C. and an excess amount (100 g) of dry-ice is added. The reaction mixture is again allowed to warm to −30° C. and stirring is continued for 2 hours at −30° C. and then at room temperature overnight. The reaction is quenched by addition of saturated aqueous ammonium chloride (500 mL). The mixture is partitioned between 1 N HCl (500 mL) and EtOAc (500 mL). The organic layer is washed with brine (400 mL), dried ($MgSO_4$) and concentrated by rotary evaporator to give crude product which is purified by flash chromatography (10:1 hexanes/methanol) to give 4-(BOC-amino)-5-trifluoromethylbenzoic acid (m.p. 197–198° C.).

2-(BOC-amino)-5-trifluoromethylbenzoic acid, obtained above (120 g) is dissolved in absolute ethanol (200 mL) and treated with 3 N HCl (80 mL). The reaction mixture is heated to reflux temperature for 3 hours and then cooled to room temperature. Most of the ethanol is removed by rotary evaporator and the pH of the remaining solution adjusted to pH 7 with 2 N NaOH solution. The mixture is extracted with EtOAc (500 mL), the organic layer is washed with brine (250 mL), dried ($MgSO_4$) and the solvent removed by rotary evaporator. The residue is purified by trituration with hexanes and filtration to give 5-trifluoromethylanthranilic acid (m.p. 191–192° C.).

5-Trifluoromethylanthranilic acid (43 g, 0.21 mol) is suspended in a mixture of concentrated HCl (40 mL) and water (240 mL), cooled to 0° C. and stirred. Sodium nitrite (18 g, 0.26 mol) is dissolved in water (50 mL) and slowly added taking care to maintain the temperature of the reaction mixture below 5° C. Stirring is continued at 0° C. for 30 minutes. Potassium iodide (65 g, 0.39 mol) is dissolved in a mixture of concentrated $H_2SO_4$ (15 mL) and water (100 mL) and the solution is added dropwise to the reaction mixture while keeping the temperature below 10° C. The mixture is then heated to 100° C. and stirred for 2 hours. After cooling to room temperature, the mixture is partitioned between EtOAc (750 mL) and saturated sodium bisulfite solution (500 mL). The organic layer is washed again with saturated sodium bisulfite solution (500 mL) and then brine (500 mL), dried ($MgSO_4$) and concentrated by rotary evaporator to give 5-trifluoromethyl-2-iodobenzoic acid (m.p. 171–172° C.).

5-Trifluoromethyl-2-iodobenzoic acid (50 g, 158 mmol) is dissolved in anhydrous THF (200 mL) and cooled in an ice-salt bath until the temperature reaches −5° C. Borane-THF complex is added dropwise as a 1.0 M solution in THF (350 mL, 350 mmol) at −5° C. After addition is complete, the reaction mixture is slowly warmed to room temperature and stirred for 12 hours. Water (40 mL) is carefully added dropwise (foaming) and the reaction mixture stirred for 30 minutes. Additional water (350 mL) is added and the mixture is concentrated by rotary evaporator to remove most of the THF. Additional water (250 mL) is added to form a precipitate, which is isolated by filtration to give 5-trifluoromethyl-2-iodobenzyl alcohol (m.p. 81–82° C.).

5-Trifluoromethyl-2-iodobenzyl alcohol (45 g, 0.15 mol) is dissolved in anhydrous $Et_2O$ (400 mL) and treated with phosphorous tribromide (41 mL, 0.15 mol) by dropwise addition. The reaction mixture is stirred at room temperature overnight and quenched by slow addition of water (150 mL). The organic layer is separated, washed with saturated aqueous $NaHCO_3$ (250 mL), brine (250 mL), dried ($MgSO_4$) and concentrated by rotary evaporator to give 5-trifluoromethyl-2-iodobenzyl bromide as an oil.

A solution of 5-trifluoromethyl-2-iodobenzyl bromide (55 g, 0.15 mol) in EtOH (200 mL) is stirred at room temperature and a solution of sodium cyanide (16 g, 0.33 mol) in water (60 mL) is added. The reaction mixture is heated to reflux temperature for 3 hours and then cooled to room temperature. Most of the ethanol is removed by rotary evaporator and the residue partitioned between EtOAc (500 mL) and water (200 mL). The organic layer is washed with brine (250 mL), dried ($MgSO_4$) and the solvent is removed by rotary evaporator. The residue is purified using flash chromatography (1:9 EtOAc/hexanes) to give 5-trifluoromethyl-2-iodophenylacetonitrile as a solid.

A solution of 5-trifluoromethyl-2-iodophenylacetonitrile (30 g, 96 mmol) in ethanol (100 mL) is stirred at room temperature. Sodium hydroxide (7.7 g, 192 mmol) dissolved in water (60 mL) is added. The mixture is heated to reflux temperature for 12 hours and then cooled to room temperature. Most of the ethanol is removed using a rotary evaporator and the residual aqueous solution adjusted to pH 4 with 3 N HCl. The solid which forms is isolated by filtration and washed with water (250 mL) and then hexanes (500 mL). Air drying gives 5-trifluoromethyl-2-iodophenylacetic acid.

5-Trifluoromethyl-2-iodophenylacetic acid (30 g, 91 mmol) is dissolved in 2-propanol (250 mL), a catalytic amount (4 drops) of concentrated $H_2SO_4$ added and the solution is stirred and heated to reflux temperature for 12 hours. Solvents are removed by rotary evaporator and the residual oil is purified using flash chromatography (1:4 EtOAc/hexanes) to give isopropyl 5-trifluoromethyl-2-iodophenylacetate as an oil.

Example 3

(a)(i)   N,N-Dimethyl-2-(2',3',5',6'-tetrafluoro-4'-phenylanilino)phenylacetamide N,N-dimethyl-2-iodophenylacetamide (2.0 g, 6.9 mmol), 2,3,5,6-tetrafluoro-4-phenylaniline (3.3 g, 13.8 mmol), copper powder (219 mg, 3.4 mmol), copper(I) iodide (646 mg, 3.4 mmol) and anhydrous potassium carbonate (1.0 g, 6.9 mmol) are stirred together in 150 mL of xylenes. The reaction is heated to reflux temperature for 48 hours. While still slightly warm (40° C.) the brown suspension is filtered through a pad of Celite which in turn is rinsed with toluene (250 mL). The filtrate is evaporated by rotary evaporator and then flash chromatographed on silica gel (10–20% EtOAc/hexane) to give the title product.

(a)(ii)   N,N-Dimethyl-5-cyclopropyl-2-[2'-fluoro-4'-(4-fluorophenyl)anilino]phenylacetamide A mixture of N,N-dimethyl-2-bromo-5-cyclopropylphenylacetamide (1.0 g), 2-fluoro-4-(4-fluorophenyl)aniline (1.5 g), $K_2CO_3$ (490 mg), KI (590 mg), Cu (113 mg), CuI (337 mg) in xylenes (10 mL) is heated to reflux for 48 hours. After cooling, the reaction is filtered through silica gel and the filtrate concentrated to a brown oil. The oil is purified by flash chromatography using 10%, then 20%, then 30%, then 40% EtOAc in hexane to give the title product as a foam.

Similarly prepared are the following compounds of the formula

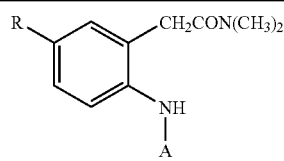

| Compound | R | A |
|---|---|---|
| (b) | Cl | 6-Cl-5-indanyl |
| (c) | Cl | 3-quinolinyl |
| (d) | H | 1-Cl-2-naphthyl |
| (e) | $CH_3$ | 1-Cl-2-naphthyl |
| (f) | Cl | 2-naphthyl |

-continued

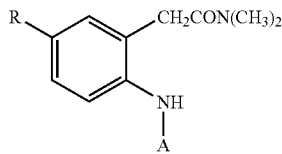

| Compound | R | A |
|---|---|---|
| (g) | Cl | 1-Cl-2-naphthyl |
| (h) | H | 2-F-4-cyclopropylphenyl |
| (i) | CH$_3$ | 2-methyl-6-quinolinyl |
| (j) | H | 4-(4-F-phenyl)-2-F-phenyl |
| (k) | H | 5-Cl-6-indanyl |
| (l) | H | 4-phenyl-2-F-phenyl |
| (m) | H | 3-quinolinyl |
| (n) | H | 2-naphthyl |
| (o) | CH$_3$ | 2-naphthyl |
| (p) | Cl | 2-Cl-4-cyclopropylphenyl |
| (q) | CH$_3$ | 2-Cl-4-cyclopropylphenyl |
| (r) | Cl | 4-phenyl-2,3,5,6-tetra-F-phenyl |
| (s) | CH$_3$ | 4-phenyl-2,3,5,6-tetra-F-phenyl |
| (t) | CH$_3$ | 2-Cl-4-cyclopropyl-6-F-phenyl |
| (u) | Cl | 4-(4-F-phenyl)-2-F-phenyl |
| (v) | H | 4-(4-CH$_3$O-phenyl)-2-Cl-phenyl |
| (w) | Cl | 4-(4-CH$_3$O-phenyl)-2-F-phenyl |
| (x) | H | 4-phenyl-2,6-di-Cl-Phenyl |
| (y) | H | 4-phenyl-2-Cl,6-F-Phenyl |
| (z) | CH$_3$ | 4-phenyl-2-Cl,6-F-phenyl |
| (aa) | CH$_3$ | 4-phenyl-2,6-di-Cl-phenyl |
| (ab) | CH$_3$ | 4-(3-CH$_3$O-phenyl)-2,3,5,6-tetra-F-phenyl |
| (ac) | Cl | 4-(3-CH$_3$O-phenyl)-2,3,5,6-tetra-F-phenyl |
| (ad) | CH$_3$ | 4-(4-F-phenyl)-2,3,5,6-tetra-F-phenyl |
| (ae) | Cl | 4-(3,4-methylenedioxyphenyl)-2,3,5,6-tetra-F-phenyl |
| (af) | CH$_3$ | 4-cyclohexyl-2-Cl-phenyl |
| (ag) | Cl | 4-cyclohexyl-2-Cl-phenyl |
| (ah) | F | 4-cyclopropyl-2-Cl-phenyl |
| (ai) | CH$_3$ | 4-cyclopropyl-2-Cl,6-F-phenyl |
| (aj) | Cl | 3-Cl-2-naphthyl |
| (ak) | CH$_3$ | 3-Cl-2-naphthyl |
| (al) | CH$_3$ | 6-CH$_3$-5-indanyl |
| (am) | CH$_3$CH$_2$ | 6-Cl-5-indanyl |
| (an) | CH$_3$ | 2-Cl-4-(5-Cl-2-thienyl)phenyl |
| (ao) | Cl | 2-Cl-4-(4-F-phenyl)phenyl |
| (ap) | CH$_3$ | 4-(3-CH$_3$O-phenyl)-2-Cl,6-F-phenyl |
| (aq) | H | 4-(3-CH$_3$O-phenyl)-2,3,5,6-tetra-F-phenyl |
| (ar) | OCH$_3$ | 4-(3-CH$_3$O-phenyl)-2,3,5,6-tetra-F-phenyl |
| (as) | H | 3-Cl-2-naphthyl |
| (at) | Cl | 4-(4-CH$_3$O-phenyl)-2-Cl-phenyl |
| (au) | CH$_3$ | 4-(4-CH$_3$O-phenyl)-2-Cl-phenyl |
| (av) | Cl | 4-(2,4-di-F-phenyl)-2-Cl-phenyl |
| (aw) | CH$_3$ | 4-(2,4-di-F-phenyl)-2-Cl-phenyl |
| (ax) | CH$_3$ | 4-(4-F-phenyl)-2-F-phenyl |
| (ay) | H | 4-cyclohexylphenyl |
| (az) | Cl | 4-(3-CH$_3$O-phenyl)-2-Cl,6-F-phenyl |
| (ba) | CH$_3$ | 4-(4-F-phenyl)-2-Cl-phenyl |
| (bb) | Cl | 4-(4-F-phenyl)-2-Br-phenyl |
| (bc) | Cl | 4-(4-Cl-phenyl)-2-F,6-Cl-phenyl |
| (bd) | Cl | 4-(4-F-phenyl)-2-F,6-Cl-phenyl |
| (be) | Cl | 4-(4-F-phenyl)-2,3,5,6-tetra-F-phenyl |
| (bf) | CH$_3$ | 4-(4-Cl-phenyl)-2-F-6-Cl-phenyl |
| (bg) | CH$_3$ | 4-(4-F-phenyl)-2-F,6-Cl-phenyl |
| (bh) | Cl | 2-(4-F-phenyl)-4-CH$_3$-phenyl |
| (bi) | Cl | 4-(4-OCF$_3$-phenyl)-2-Cl-phenyl |
| (bj) | CH$_3$ | 4-(4-Cl-phenyl)-2,3,5,6-tetra-F-phenyl |
| (bk) | Cl | 4-(4-Cl-phenyl)-2,3,5,6-tetra-F-phenyl |
| (bl) | Cl | 4-(2-OCH$_3$-phenyl)-2-Cl-phenyl |
| (bm) | CH$_3$ | 4-(4-F-phenyl)-2,3,5,6-tetra-F-phenyl |
| (bn) | Cl | 4-(4-F-phenyl)-2,6-di-Cl-phenyl |
| (bo) | CH$_3$ | 4-(4-F-phenyl)-2,6-di-Cl-phenyl |
| (bp) | CH$_3$ | 4-(2-OCH$_3$-phenyl)-2-Cl-phenyl |
| (bq) | Cl | 4-(4-OCH$_3$-phenyl)-2-F,6-Cl-phenyl |
| (br) | CH$_3$ | 4-(4-OCH$_3$-phenyl)-2-F,6-Cl-phenyl |
| (bs) | cyclopropyl | 4-(4-F-phenyl)-2,3,5,6-tetra-F-phenyl |
| (bt) | CH$_3$ | 4-(4-Cl-phenyl)-2,6-di-Cl-phenyl |
| (bu) | CH$_3$ | 4-(4-F-phenyl)-2,6-di-F-phenyl |
| (bv) | CH$_3$CH$_2$ | 4-cyclopropyl-2-F,6-Cl-phenyl |

-continued

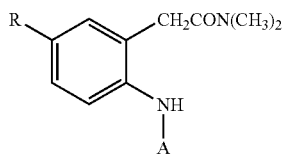

| Compound | R | A |
| --- | --- | --- |
| (bw) | Cl | 4-cyclopropyl-2-F,6-Cl-phenyl |
| (bx) | Cl | 4-(4-Cl-phenyl)-2,3,6-tri-F-phenyl |
| (by) | Cl | 4-(4-F-phenyl)-2,3,6-tri-F-phenyl |
| (bz) | Cl | 4-(4-Cl-phenyl)-2,6-di-F-phenyl |
| (ca) | Cl | 4-(4-F-phenyl)-2,6-di-F-phenyl |
| (cb) | $CH_3CH_2$ | 4-cyclopropyl-2,3,5,6-tetra-F-phenyl |
| (cc) | Cl | 4-cyclopropyl-2,3,5,6-tetra-F-phenyl |
| (cd) | cyclopropyl | 4-cyclopropyl-2-F,6-Cl-phenyl |
| (ce) | cyclopropyl | 4-cyclopropyl-2,3,5,6-tetra-F-phenyl |
| (cf) | $CH_3$ | 4-cyclopropyl-2,3,6-tri-F-phenyl |
| (cg) | $CH_3$ | 4-cyclopropyl-2,3,5,6-tetra-F-phenyl |
| (ch) | cyclopropyl | 4-(3-$OCH_3$-phenyl)-2,3,5,6-tetra-F-phenyl |
| (ci) | $CH_3CH_2$ | 4-(3-$OCH_3$-phenyl)-2,3,5,6-tetra-F-phenyl |
| (cj) | $CH_3$ | 4-(3-OH-phenyl)-2-F,6-Cl-phenyl |
| (ck) | Cl | 4-(3,4-methylenedioxy-phenyl)-2-F,6-Cl-phenyl |
| (cl) | $CH_3$ | 4-(3,4-methylenedioxy-phenyl)-2-F,6-Cl-phenyl |
| (cm) | $CH_3CH_2$ | 4-cyclopropyl-2,3,6-tri-F-phenyl |
| (cn) | $CH_3$ | 4-(3-$OCH_3$-phenyl)-2-F,6-$CF_3$-phenyl |
| (co) | $CH_3$ | 4-(3-OH-phenyl)-2,3,5,6-tetra-F-phenyl |
| (cp) | cyclopropyl | 4-(3-$OCH_3$-phenyl)-2-F,6-Cl-phenyl |
| (cq) | Cl | 4-cyclopropyl-2,3,6-tri-F-phenyl |
| (cr) | Cl | 4-(4-$OCF_3$-phenyl)-2-F,6-Cl-phenyl |
| (cs) | $CH_3CH_2$ | 4-(3-OH-phenyl)-2,3,5,6-tetra-F-phenyl |
| (ct) | $CH_3CH_2$ | 4-(3-$OCH_3$-phenyl)-2-F,6-Cl-phenyl |
| (cu) | $CH_3CH_2$ | 4-(3,4-methylenedioxy-phenyl)-2-F,6-Cl-phenyl |
| (cv) | $CH_3CH_2$ | 4-(3-$OCH_3$-phenyl)-2-F,3-$CH_3$,6-Cl-phenyl |
| (cw) | $CH_3$ | 4-(3-$OCH_3$-phenyl)-2-F,3-$CH_3$,6-Cl-phenyl |
| (cx) | $CH_3CH_2$ | 4-(4-$OCH_3$-phenyl)-2-F,3-$CH_3$,6-Cl-phenyl |
| (cy) | $CH_3$ | 4-(4-$OCH_3$-phenyl)-2-F,3-$CH_3$,6-Cl-phenyl |
| (cz) | $CH_3CH_2$ | 4-(2,4-di-$OCH_3$-phenyl)-2-F,6-Cl-phenyl |
| (da) | $CH_3$ | 4-(2,4-di-$OCH_3$-phenyl)-2-F,6-Cl-phenyl |
| (db) | $CH_3CH_2$ | 4-(2,4-di-$OCH_3$-phenyl)-2,3,5,6-tetra-F-phenyl |
| (dc) | $CH_3$ | 4-(2,4-di-$OCH_3$-phenyl)-2,3,5,6-tetra-F-phenyl |
| (dd) | $CH_3CH_2$ | 4-cyclopropyl-2-Cl,5-$OCH_3$-phenyl |
| (de) | $CH_3$ | 4-cyclopropyl-2-Cl,5-$OCH_3$-phenyl |
| (df) | $CH_3$ | 4-cyclopropyl-2-F,3-$CH_3$,6-Cl-phenyl |
| (dg) | Cl | 4-(2,4-di-$OCH_3$-phenyl)-2,3,5,6-tetra-F-phenyl |
| (dh) | Cl | 4-cyclopropyl-2-Cl,5-$OCH_3$-phenyl |
| (di) | $CH_3CH_2$ | 4-cyclopropyl-2-F,3-$CH_3$,6-Cl-phenyl |
| (dj) | Cl | 4-cyclopropyl-2-F,3-$CH_3$,6-Cl-phenyl |
| (dk) | $CH_3CH_2$ | 4-(4-hydroxyphenyl)-2-F,6-Cl-phenyl |
| (dl) | cyclopropyl | 4-cyclopropyl-2,3,6-tri-F-phenyl |
| (dm) | $CH_3$ | 4-cyclopropyl-2-F,3-$CF_3$-phenyl |
| (dn) | $CH_3CH_2$ | 4-cyclopropyl-2-F,3-$CF_3$-phenyl |
| (d ) | $CH_3$ | 4-(4-hydroxyphenyl)-2-F-3-$CH_3$,6-Cl-phenyl |
| (dp) | Cl | 4-cyclopropyl-2,4-di-F,3-$CH_3$,6-Cl-phenyl |
| (dq) | $CH_3$ | 4-cyclopropyl-2,4-di-F,3-$CH_3$,6-Cl-phenyl |
| (dr) | Cl | 4-(2,4-di-$OCH_3$-phenyl)-2-F,6-Cl-phenyl |
| (ds) | $CH_3$ | 4-(4-$CF_3$O-phenyl)-2-F,6-Cl-phenyl |
| (dt) | Cl | 4-cyclopropyl-2,3-di-F,6-Cl-phenyl |
| (du) | $CH_3CH_2$ | 4-cyclopropyl-2,3-di-F,6-Cl-phenyl |
| (dv) | $CH_3$ | 4-cyclopropyl-2,3-di-F,6-Cl-phenyl |
| (dw) | $CH_3CH_2$ | 4-(4-$CF_3$O-phenyl)-2,6-di-F-phenyl |
| (dx) | $CH_3$ | 4-(4-$CF_3$O-phenyl)-2,6-di-F-phenyl |
| (dy) | $CH_3CH_2$ | 4-(4-$CF_3$O-phenyl)-2-F,6-Cl-phenyl |
| (dz) | Cl | 4-(4-$CF_3$O-phenyl)-2,6-di-F-phenyl |
| (ea) | $CH_3$ | 4-cyclopropyl-2,6-di-F-phenyl |
| (eb) | $CH_3CH_2$ | 4-cyclopropyl-2,6-di-F-phenyl |
| (ec) | cyclopropyl | 4-cyclopropyl-2,3-di-F,6-Cl-phenyl |
| (ed) | Cl | 4-cyclopropyl-2,6-di-F-phenyl |
| (ee) | cyclopropyl | 4-cyclopropyl-2,6-di-F-phenyl |
| (ef) | $CH_3$ | 4-cyclopropyl-2-F,5-$CF_3$-phenyl |
| (eg) | $CH_3CH_2$ | 4-cyclopropyl-2-F,5-$CF_3$-phenyl |

-continued

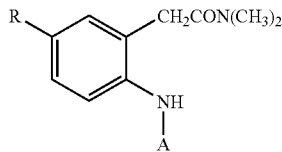

| Compound | R | A |
|---|---|---|
| (eh) | CH$_3$ | 4-cyclopropyl-2,5-di-F,6-Cl-phenyl |
| (ei) | Cl | 4-cyclopropyl-2,5-di-F,6-Cl-phenyl |
| (ej) | CH$_3$CH$_2$ | 4-cyclopropyl-2,5-di-F,6-Cl-phenyl |
| (ek) | CH$_3$CH$_2$ | 1-Cl-2-naphthyl |
| (el) | Cl | 1-Cl-6-F-2-naphthyl |
| (em) | Cl | 1-6-di-Cl-2-naphthyl |
| (en) | Cl | 1,3-di-Cl-2-naphthyl |
| (eo) | cyclopropyl | 1-Cl-2-naphthyl |
| (ep) | CH$_3$ | 1-Cl,6-F-2-naphthyl |
| (eq) | CH$_3$CH$_2$ | 1-Cl,6-F-2-naphthyl |
| (er) | Cl | 1-F-2-naphthyl |
| (es) | CH$_3$ | 1-F-2-naphthyl |
| (et) | cyclopropyl | 1-Cl,6-F-2-naphthyl |
| (eu) | Cl | 1-Cl,3-F-2-naphthyl |
| (ev) | cyclopropyl | 7-CF$_3$-4-quinolinyl |
| (ew) | Cl | 7-Cl-4-quinolinyl |
| (ex) | CH$_3$ | 7-Cl-4-quinolinyl |
| (ey) | Cl | 2,7-di-CF$_3$-4-quinolinyl |
| (ez) | Cl | 6-OCH$_3$-8-quinolinyl |
| (fa) | Cl | 1-Cl,7-F-2-naphthyl |
| (fb) | Cl | 1-Cl,7-CF$_3$-2-naphthyl |
| (fc) | cyclopropyl | 4-cyclopropyl-2,5-di-F,6-Cl-phenyl |
| (fd) | CH$_3$CH$_2$ | 4-(3,4-methylenedioxypheny)-2,6-di-F-phenyl |
| (fe) | Cl | 4-(3,4-methylenedioxypheny)-2,6-di-F-phenyl |
| (ff) | CH$_3$ | 4-(3,4-methylenedioxypheny)-2,6-di-F-phenyl |
| (fg) | Cl | 4-cyclopropyl-2-F,5-CF$_3$-phenyl |
| (fh) | cyclopropyl | 4-cyclopropyl-2-F,5-CF$_3$-phenyl |
| (fi) | cyclopropyl | 4-cyclopropyl-2-Cl,3,6-di-F,5-CH$_3$-phenyl |
| (fj) | CH$_3$CH$_2$ | 4-cyclopropyl-2-Cl,3,6-di-F,5-CH$_3$-phenyl |
| (fk) | CH$_3$CH$_2$ | 4-cyclopropyl-2-Cl,5-F-phenyl |
| (fl) | CH$_3$ | 4-cyclopropyl-2-Cl,5-F-phenyl |
| (fm) | Cl | 4-cyclopropyl-2-Cl,5-F-phenyl |
| (fn) | cyclopropyl | 4-cyclopropyl-2-Cl,5-F-phenyl |
| (fo) | cyclopropyl | 4-cyclopropyl-2-F,5-Cl-phenyl |
| (fp) | CH$_3$ | 3-cyclopropyl-2-F,4-CH$_3$,6-Cl-phenyl |
| (fq) | CH$_3$ | 2-cyclopropyl-4-Cl,6-F-phenyl |
| (fr) | CH$_3$ | 8-CF$_3$-4-quinolinyl |
| (fs) | CH$_3$ | 7-Cl,2-CF$_3$-4-quinolinyl |
| (ft) | CH$_3$ | 6-F,2-CF$_3$-4-quinolinyl |
| (fu) | CH$_3$ | 1-F,3-Cl-2-naphthyl |
| (fv) | CH$_3$CH$_2$ | 3-Cl-2-naphthyl |
| (fw) | Cl | 1-Cl,6-F-2-naphthyl |
| (fx) | Cl | 1-F,3-Cl-2-naphthyl |
| (fy) | CH$_3$ | 1-Cl,3-F-2-naphthyl |
| (fz) | CH$_3$ | 1,3-di-F-2-naphthyl |
| (ga) | Cl | 1,3-di-F-2-naphthyl |
| (gb) | CH$_3$CH$_2$ | 3-cyclopropyl-2-F,4-CH$_3$,6-Cl-phenyl |
| (gc) | Cl | 3-cyclopropyl-2-F,4-CH$_3$,6-Cl-phenyl |
| (gd) | cyclopropyl | 4-cyclopropyl-2-Cl,3,5-di-F-phenyl |
| (ge) | CH$_3$ | 4-cyclopropyl-2-Cl,5-CH$_3$-phenyl |
| (gf) | Cl | 4-cyclopropyl-2-Cl,5-CH$_3$-phenyl |
| (gg) | CH$_3$CH$_2$ | 4-cyclopropyl-2-Cl,5-CH$_3$-phenyl |
| (gh) | cyclopropyl | 4-cyclopropyl-2-Cl,5-CH$_3$-phenyl |
| (gi) | cyclopropyl | 4-cyclopropyl-2-F,3-CH$_3$,6-Cl-phenyl |
| (gj) | CH$_3$ | 4-cyclopropyl-2-Cl,3,5-di-F-phenyl |
| (gk) | CH$_3$CH$_2$ | 4-cyclopropyl-2-Cl,3,5-di-F-phenyl |
| (gl) | Cl | 4-cyclopropyl-2-Cl,3,5-di-F-phenyl |

Example 4

(a)(i) 2-(2',3',5',6'-Tetrafluoro-4'-phenylanilino)phenylacetic Acid

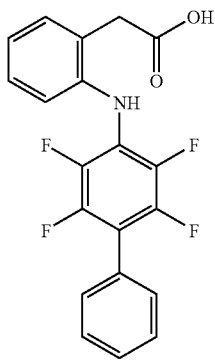

A mixture of N,N-dimethyl-2-(2',3',5',6'-tetrafluoro-4'-phenylanilino)phenylacetamide (2.7 g, 6.7 mmol) and NaOH (3.0 g, 72 mmol) in EtOH (100 mL) and water (20 mL) is heated at reflux temperature for 14 hours. After cooling to room temperature, most of the ethanol is removed by rotary evaporator. Ice water (250 mL) and ice cold $Et_2O$ (250 mL) are added and the organic phase is separated and washed with ice cold 1 N HCl (200 mL) and then brine (100 mL). The organic solution is dried ($MgSO_4$) and evaporated by rotary evaporator taking care not to warm above 50° C. The title compound is obtained by trituration of the residue with hexane (m.p. 180–181° C.).

(a)(ii) 5-Cyclopropyl-2-[2'-fluoro-4'-(4-fluorophenyl)anilino]phenylacetic Acid

A solution of N,N-dimethyl-5-cyclopropyl-2-[2'-fluoro-4'-(4-fluorophenyl)anilino]phenylacetamide (575 mg) in 10 mL of 4 N NaOH and 20 mL of EtOH is heated overnight at 80° C. After cooling, the EtOH is removed under reduced pressure and the residue is diluted with EtOAc and cold water. The mixture is cooled in an ice bath and cold 2.5 N HCl is added until the pH of the aqueous layer reaches 2. The organic phase is separated, washed with brine, dried ($Na_2SO_4$) and concentrated in vacuo to give a brown solid. The solid is purified by flash chromatography eluting with 10%, then 20%, then 30% EtOAc in hexane to give the title product, m.p. 182–183° C.

Similarly prepared are the following compounds of the formula

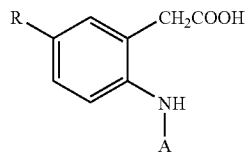

| Compound | R | A | m.p., MS |
|---|---|---|---|
| (b) | Cl | 6-Cl-5-indanyl | 132–134° C. |
| (c) | Cl | 3-quinolinyl | 193–195° C. |
| (d) | H | 1-Cl-2-naphthyl | 156–158° C. |
| (e) | $CH_3$ | 1-Cl-2-naphthyl | 141–143° C. |
| (f) | Cl | 2-naphthyl | 128–130° C. |
| (g) | Cl | 1-Cl-2-naphthyl | 156–158° C. |
| (h) | H | 2-F-4-cyclopropylphenyl | 104–105° C. |
| (i) | $CH_3$ | 2-methyl-6-quinolinyl | 172–175° C. |
| (j) | H | 4-(4-F-phenyl)-2-F-phenyl | M − 1 = 338, M + 1 = 340 |
| (k) | H | 6-Cl-5-indanyl | 133–134° C. |
| (l) | H | 4-phenyl-2-F-phenyl | M − 1 = 320, M + 1 = 322 |
| (m) | H | 3-quinolinyl | 182–184° C. |
| (n) | H | 2-naphthyl | 131–133° C. |
| (o) | $CH_3$ | 2-naphthyl | 130–132° C. |
| (p) | Cl | 2-Cl-4-cyclopropylphenyl | 128–129° C. |
| (q) | $CH_3$ | 2-Cl-4-cyclopropylphenyl | 114–116° C. |
| (r) | Cl | 4-phenyl-2,3,5,6-tetra-F-phenyl | 181–182° C. |
| (s) | $CH_3$ | 4-phenyl-2,3,5,6-tetra-F-phenyl | 156–157° C. |
| (t) | $CH_3$ | 2-Cl-4-cyclopropyl-6-F-phenyl | M − 1 = 332, M + 1 = 334 |
| (u) | Cl | 4-(4-F-phenyl)-2-F-phenyl | M − 1 = 372, M + 1 = 374 |
| (v) | H | 4-(4-$OCH_3$-phenyl)-2-Cl-phenyl | 150–151° C. |
| (w) | Cl | 4-(4-$OCH_3$-phenyl)-2-F-phenyl | 100–102° C. |
| (x) | H | 4-phenyl-2,6-di-Cl-phenyl | 191–192° C. |
| (y) | H | 4-phenyl-2-Cl,6-F-phenyl | 162–163° C. |
| (z) | $CH_3$ | 4-phenyl-2-Cl,6-F-phenyl | 176–177° C. |
| (aa) | $CH_3$ | 4-phenyl-2,6-di-Cl-phenyl | 177–178° C. |
| (ab) | $CH_3$ | 4-(3-$CH_3O$-phenyl)-2,3,5,6-tetra-F-phenyl | 164–166° C. |
| (ac) | Cl | 4-(3-$CH_3O$-phenyl)-2,3,5,6-tetra-F-phenyl | 171–173° C. |
| (ad) | $CH_3$ | 4-(4-F-phenyl)-2,3,5,6-tetra-F-phenyl | 155–158° C. |
| (ae) | Cl | 4-(3,4-methylenedioxyphenyl)-2-3,5,6-tetra-F-phenyl | M − 1 = 452 |
| (af) | $CH_3$ | 4-cyclohexyl-2-Cl-phenyl | 133–135° C. |

-continued

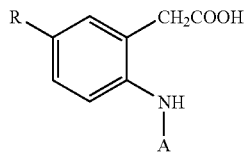

| Compound | R | A | m.p., MS |
|---|---|---|---|
| (ag) | Cl | 4-cyclohexyl-2-Cl-phenyl | 134–136° C. |
| (ah) | F | 4-cyclopropyl-2-Cl-phenyl | M − 1 = 318, M + 1 = 320 |
| (ai) | CH$_3$ | 4-cyclopropyl-2-Cl,6-F-phenyl | M − 1 = 332, M + 1 = 334 |
| (aj) | Cl | 3-Cl-2-naphthyl | 168–170° C. |
| (ak) | CH$_3$ | 3-Cl-2-naphthyl | 152–154° C. |
| (al) | CH$_3$ | 6-CH$_3$-5-indanyl | 108–110° C. |
| (am) | CH$_3$CH$_2$ | 6-Cl-5-indanyl | 135–137° C. |
| (an) | CH$_3$ | 2-Cl-4-(5-Cl-2-thienyl)phenyl | 141–143° C. |
| (ao) | Cl | 2-Cl-4-(4-F-phenyl)phenyl | 127–128° C. |
| (ap) | CH$_3$ | 4-(3-CH$_3$O-phenyl)-2-Cl,6-F-phenyl | 150–152° C. |
| (aq) | H | 4-(3-CH$_3$O-phenyl)-2,3,5,6-tetra-F-phenyl | 160–162° C. |
| (ar) | OCH$_3$ | 4-(3-CH$_3$O-phenyl)-2,3,5,6-tetra-F-phenyl | 141–143° C. |
| (as) | H | 3-chloro-2-naphthyl | 153–155° C. |
| (at) | Cl | 4-(4-CH$_3$O-phenyl)-2-Cl-phenyl | 154–155° C. |
| (au) | CH$_3$ | 4-(4-CH$_3$O-phenyl)-2-Cl-phenyl | 142–144° C. |
| (av) | Cl | 4-(2,4-di-F-phenyl)-2-Cl-phenyl | 220–222° C. |
| (aw) | CH$_3$ | 4-(2,4-di-F-phenyl)-2-Cl-phenyl | 135–138° C. |
| (ax) | CH$_3$ | 4-(4-F-phenyl)-2-F-phenyl | 128–130° C. |
| (ay) | H | 4-cyclohexylphenyl | 108–110° C. |
| (az) | Cl | 4-(3-CH$_3$O-phenyl)-2-Cl,6-F-phenyl | 170–172° C. |
| (ba) | CH$_3$ | 4-(4-F-phenyl)-2-Cl-phenyl | 142–143° C. |
| (bb) | Cl | 4-(4-F-phenyl)-2-Br-phenyl | 97–101° C. |
| (bc) | Cl | 4-(4-Cl-phenyl)-2-F,6-Cl-phenyl | 172–174° C. |
| (bd) | Cl | 4-(4-F-phenyl)-2-F,6-Cl-phenyl | 199–200° C. |
| (be) | Cl | 4-(4-F-phenyl)-2,3,5,6-tetra-F-phenyl | 175–177° C. |
| (bf) | CH$_3$ | 4-(4-Cl-phenyl)-2-F,6-Cl-phenyl | 195–197° C. |
| (bg) | CH$_3$ | 4-(4-F-phenyl)-2-F,6-Cl-phenyl | 159–161° C. |
| (bh) | Cl | 2-(4-F-phenyl)-4-CH$_3$-phenyl | 138–140° C. |
| (bi) | Cl | 4-(4-OCF$_3$-phenyl)-2-Cl-phenyl | 142–144° C. |
| (bj) | CH$_3$ | 4-(4-Cl-phenyl)-2,3,5,6-tetra-F-phenyl | 142–145° C. |
| (bk) | Cl | 4-(4-Cl-phenyl)-2,3,5,6-tetra-F-phenyl | 167–168° C. |
| (bl) | Cl | 4-(2-OCH$_3$-phenyl)-2-Cl-phenyl | 126–128° C. |
| (bm) | CH$_3$ | 4-(4-F-phenyl)-2,3,5,6-tetra-F-phenyl | 222–224° C. |
| (bn) | Cl | 4-(4-F-phenyl)-2,6-di-Cl-phenyl | 168–170° C. |
| (bo) | CH$_3$ | 4-(4-F-phenyl)-2,6-di-Cl-phenyl | 138–140° C. |
| (bp) | CH$_3$ | 4-(2-OCH$_3$-phenyl)-2-Cl-phenyl | 70–73° C. |
| (bq) | Cl | 4-(4-OCH$_3$-phenyl)-2-F,6-Cl-phenyl | 139–140° C. |
| (br) | CH$_3$ | 4-(4-OCH$_3$-phenyl)-2-F,6-Cl-phenyl | 137–138° C. |
| (bs) | cyclopropyl | 4-(4-F-phenyl)-2,3,5,6-tetra-F-phenyl | 158–160° C. |
| (bt) | CH$_3$ | 4-(4-Cl-phenyl)-2,6-di-Cl-phenyl | 139–140° C. |
| (bu) | CH$_3$ | 4-(4-F-phenyl)-2,6-di-F-phenyl | 129–130° C. |
| (bv) | CH$_3$CH$_2$ | 4-cyclopropyl-2,6-Cl-phenyl | 154–155° C. |
| (bw) | Cl | 4-cyclopropyl-2-F,6-Cl-phenyl | 156–158° C. |
| (bx) | Cl | 4-(4-Cl-phenyl)-2,3,6-tri-F-phenyl | 160–162° C. |
| (by) | Cl | 4-(4-F-phenyl)-2,3,6-tri-F-phenyl | 173–176° C. |
| (bz) | Cl | 4-(4-Cl-phenyl)-2,6-di-F-phenyl | 217–220° C. |
| (ca) | Cl | 4-(4-F-phenyl)-2,6-di-F-phenyl | 206–208° C. |
| (cb) | CH$_3$CH$_2$ | 4-cyclopropyl-2,3,5,6-tetra-F-phenyl | 138–140° C. |
| (cc) | Cl | 4-cyclopropyl-2,3,5,6-tetra-F-phenyl | 128–130° C. |
| (cd) | cyclopropyl | 4-cyclopropyl-2-F,6-Cl-phenyl | 148–150° C. |
| (ce) | cyclopropyl | 4-cyclopropyl-2,3,5,6-tetra-F-phenyl | 137–138° C. |
| (cf) | CH$_3$ | 4-cyclopropyl-2,3,6-tri-F-phenyl | 152–153° C. |
| (cg) | CH$_3$ | 4-cyclopropyl-2,3,5,6-tetra-F-phenyl | 139–140° C. |
| (ch) | cyclopropyl | 4-(3-OCH$_3$-phenyl)-2,3,5,6-tetra-F-phenyl | 126–128° C. |
| (ci) | CH$_3$CH$_2$ | 4-(3-OCH$_3$-phenyl)-2,3,5,6-tetra-F-phenyl | |
| (cj) | CH$_3$ | 4-(3-OH-phenyl)-2-F,6-Cl-phenyl | 163–165° C. |
| (ck) | Cl | 4-(3,4-methylenedioxy-phenyl)-2-F,6-Cl-phenyl | 169–171° C. |
| (cl) | CH$_3$ | 4-(3,4-methylenedioxy-phenyl)-2-F,6-Cl-phenyl | 135–137° C. |
| (cm) | CH$_3$CH$_2$ | 4-cyclopropyl-2,3,6-tri-F-phenyl | 140–142° C. |
| (cn) | CH$_3$ | 4-(3-OCH$_3$-phenyl)-2-F,6-CF$_3$-phenyl | 169–171° C. |
| (co) | CH$_3$ | 4-(3-OH-phenyl)-2,3,5,6-tetra-F-phenyl | 166–168° C. |
| (cp) | cyclopropyl | 4-(3-OCH$_3$-phenyl)-2-F,6-Cl-phenyl | 141–143° C. |
| (cq) | Cl | 4-cyclopropyl-2,3,6-tri-F-phenyl | 142–144° C. |
| (cr) | Cl | 4-(4-OCF$_3$-phenyl)-2-F,6-Cl-phenyl | 159–160° C. |
| (cs) | CH$_3$CH$_2$ | 4-(3-OH-phenyl)-2,3,5,6-tetra-F-phenyl | 154–156° C. |

-continued

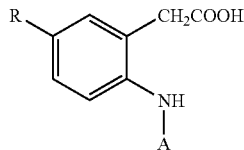

| Compound | R | A | m.p., MS |
|---|---|---|---|
| (ct) | CH$_3$CH$_2$ | 4-(3-OCH$_3$-phenyl)-2-F,6-Cl-phenyl | 136–138° C. |
| (cu) | CH$_3$CH$_2$ | 4-(3,4-methylenedioxy-phenyl)-2-F,6-Cl-phenyl | 172–174° C. |
| (cv) | CH$_3$CH$_2$ | 4-(3-OCH$_3$-phenyl)-2-F,3-CH$_3$,6-Cl-phenyl | 114–116° C. |
| (cw) | CH$_3$ | 4-(3-OCH$_3$-phenyl)-2-F,3-CH$_3$,6-Cl-phenyl | 129–131° C. |
| (cx) | CH$_3$CH$_2$ | 4-(4-OCH$_3$-phenyl)-2-F,3-CH$_3$,6-Cl-phenyl | 140–142° C. |
| (cy) | CH$_3$ | 4-(4-OCH$_3$-phenyl)-2-F,3-CH$_3$,6-Cl-phenyl | 151–153° C. |
| (cz) | CH$_3$CH$_2$ | 4-(2,4-di-OCH$_3$-phenyl)-2-F,6-Cl-phenyl | 140–142° C. |
| (da) | CH$_3$ | 4-(2,4-di-OCH$_3$-phenyl)-2-F,6-Cl-phenyl | 131–133° C. |
| (db) | CH$_3$CH$_2$ | 4-(2,4-di-OCH$_3$-phenyl)-2,3,5,6-tetra-F-phenyl | 113–115° C. |
| (dc) | CH$_3$ | 4-(2,4-di-OCH$_3$-phenyl)-2,3,5,6-tetra-F-phenyl | 153–155° C. |
| (dd) | CH$_3$CH$_2$ | 4-cyclopropyl-2-Cl,5-OCH$_3$-phenyl | 150–152° C. |
| (de) | CH$_3$ | 4-cyclopropyl-2-Cl,5-OCH$_3$-phenyl | 100–102° C. |
| (df) | CH$_3$ | 4-cyclopropyl-2-F,3-CH$_3$,6-Cl-phenyl | 136–138° C. |
| (dg) | Cl | 4-(2,4-di-OCH$_3$-phenyl)-2,3,5,6-tetra-F-phenyl | 156–158° C. |
| (dh) | Cl | 4-cyclopropyl-2-Cl,5-OCH$_3$-phenyl | 110–112° C. |
| (di) | CH$_3$CH$_2$ | 4-cyclopropyl-2-F,3-CH$_3$,6-Cl-phenyl | 132–133° C. |
| (dj) | Cl | 4-cyclopropyl-2-F,3-CH$_3$,6-Cl-phenyl | 121–123° C. |
| (dk) | CH$_3$CH$_2$ | 4-(4-hydroxyphenyl)-2-F,6-Cl-phenyl | 126–128° C. |
| (dl) | cyclopropyl | 4-cyclopropyl-2,3-6-tri-F-phenyl | 126–128° C. |
| (dm) | CH$_3$ | 4-cyclopropyl-2-F,3-CF$_3$-phenyl | 154–155° C. |
| (dn) | CH$_3$CH$_2$ | 4-cyclopropyl-2-F,3-CF$_3$-phenyl | 158–160° C. |
| (do) | CH$_3$ | 4-(4-hydroxyphenyl)-2-F,3-CH$_3$,6-Cl-phenyl | 146–148° C. |
| (dp) | Cl | 4-cyclopropyl-2,4-di-F,3-CH$_3$,6-Cl-phenyl | 159–160° C. |
| (dq) | CH$_3$ | 4-cyclopropyl-2,4-di-F,3-CH$_3$,6-Cl-phenyl | 148–150° C. |
| (dr) | Cl | 4-(2,4-di-OCH$_3$-phenyl)-2-F,6-Cl-phenyl | 139–141° C. |
| (ds) | CH$_3$ | 4-(4-CF$_3$O-phenyl)-2-F,6-Cl-phenyl | 158–159° C. |
| (dt) | Cl | 4-cyclopropyl-2,3-di-F,6-Cl-phenyl | 144–146° C. |
| (du) | CH$_3$CH$_2$ | 4-cyclopropyl-2,3-di-F,6-Cl-phenyl | 157–158° C. |
| (dv) | CH$_3$ | 4-cyclopropyl-2,3-di-F,6-Cl-phenyl | 147–148° C. |
| (dw) | CH$_3$CH$_2$ | 4-(4-CF$_3$O-phenyl)-2,6-di-F-phenyl | 158–159° C. |
| (dx) | CH$_3$ | 4-(4-CF$_3$O-phenyl)-2,6-di-F-phenyl | 179–180° C. |
| (dy) | CH$_3$CH$_2$ | 4-(4-CF$_3$O-phenyl)-2-F,6-Cl-phenyl | 157–158° C. |
| (dz) | Cl | 4-(4-CF$_3$O-phenyl)-2,6-di-F-phenyl | 163–164° C. |
| (ea) | CH$_3$ | 4-cyclopropyl-2,6-di-F-phenyl | 128–130° C. |
| (eb) | CH$_3$CH$_2$ | 4-cyclopropyl-2,6-di-F-phenyl | 136–137° C. |
| (c) | cyclopropyl | 4-cyclopropyl-2,3-di-F,6-Cl-phenyl | 156–157° C. |
| (d) | Cl | 4-cyclopropyl-2,6-di-F-phenyl | 133–135° C. |
| (ee) | cyclopropyl | 4-cyclopropyl-2,6-di-F-phenyl | 128–129° C. |
| (ef) | CH$_3$ | 4-cyclopropyl-2-F,5-CF$_3$-phenyl | 93–95° C. |
| (eg) | CH$_3$CH$_2$ | 4-cyclopropyl-2-F,5-CF$_3$-phenyl | 101–102° C. |
| (eh) | CH$_3$ | 4-cyclopropyl-2,5-di-F,6-Cl-phenyl | 162–163° C. |
| (ei) | Cl | 4-cyclopropyl-2,5-di-F,6-Cl-phenyl | 158–160° C. |
| (ej) | CH$_3$CH$_2$ | 4-cyclopropyl-2,5-di-F,6-Cl-phenyl | 156–157° C. |
| (ek) | CH$_3$CH$_2$ | 1-Cl-2-naphthyl | 132–134° C. |
| (el) | Cl | 1-Cl-6-F-2-naphthyl | 202–204° C. |
| (em) | Cl | 1,6-di-Cl-2-naphthyl | 176–178° C. |
| (en) | Cl | 1,3-di-Cl-2-naphthyl | 176–178° C. |
| (eo) | cyclopropyl | 1-Cl-2-naphthyl | 122–124° C. |
| (p) | CH$_3$ | 1-Cl,6-F-2-naphthyl | 180–182° C. |
| (eq) | CH$_3$CH$_2$ | 1-Cl,6-F-2-naphthyl | 176–178° C. |
| (er) | Cl | 1-F-2-naphthyl | 134–136° C. |
| (s) | CH$_3$ | 1-F-2-naphthyl | 126–128° C. |
| (et) | cyclopropyl | 1-Cl,6-F-2-naphthyl | 172–174° C. |
| (eu) | Cl | 1-Cl,3-F-2-naphthyl | 180–182° C. |
| (ev) | cyclopropyl | 7-CF$_3$-4-quinolinyl | 215–217° C. |
| (ew) | Cl | 7-Cl-4-quinolinyl | 292–293° C. |
| (ex) | CH$_3$ | 7-Cl-4-quinolinyl | 317–319° C. |
| (ey) | Cl | 2,7-di-CF$_3$-4-quinolinyl | 231–233° C. |
| (ez) | Cl | 6-OCH$_3$-8-quinolinyl | 133–135° C. |
| (fa) | Cl | 1-Cl,7-F-2-naphthyl | 183–185° C. |
| (fb) | Cl | 1-Cl,7-CF$_3$-2-naphthyl | 183–184° C. |
| (fc) | cyclopropyl | 4-cyclopropyl-2,5-di-F,6-Cl-phenyl | 152–153° C. |
| (fd) | CH$_3$CH$_2$ | 4-(3,4-methylenedioxypheny)-2,6-di-F-phenyl | 156–157° C. |

-continued

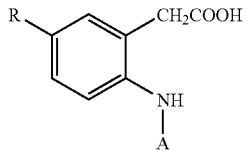

| Compound | R | A | m.p., MS |
|---|---|---|---|
| (fe) | Cl | 4-(3,4-methylenedioxypheny)-2,6-di-F-phenyl | 163–164° C. |
| (ff) | $CH_3$ | 4-(3,4-methylenedioxypheny)-2,6-di-F-phenyl | 144–145° C. |
| (fg) | Cl | 4-cyclopropyl-2-F,5-$CF_3$-phenyl | 118–119° C. |
| (fh) | cyclopropyl | 4-cyclopropyl-2-F,5-$CF_3$-phenyl | 119–120° C. |
| (fi) | cyclopropyl | 4-cyclopropyl-2-Cl-3,6-di-F-5-$CH_3$-phenyl | 141–143° C. |
| (fj) | $CH_3CH_2$ | 4-cyclopropyl-2-Cl,3,6-di-F,5-$CH_3$phenyl | 132–134° C. |
| (fk) | $CH_3CH_2$ | 4-cyclopropyl-2-Cl,5-F-phenyl | 112–114° C. |
| (fl) | $CH_3$ | 4-cyclopropyl-2-Cl,5-F-phenyl | 128–130° C. |
| (fm) | Cl | 4-cyclopropyl-2-Cl,5-F-phenyl | 152–153° C. |
| (fn) | cyclopropyl | 4-cyclopropyl-2-Cl,5-F-phenyl | 126–127° C. |
| (fo) | cyclopropyl | 4-cyclopropyl-2-F,5-Cl-phenyl | 124–125° C. |
| (fp) | $CH_3$ | 3-cyclopropyl-2-F,4-$CH_3$,6-Cl-phenyl | 144–147° C. |
| (fq) | $CH_3$ | 2-cyclopropyl-4-Cl,6-F-phenyl | 130–132° C. |
| (fr) | $CH_3$ | 8-$CF_3$-4-quinolinyl | 158–160° C. |
| (fs) | $CH_3$ | 7-Cl,2-$CF_3$-4-quinolinyl | 221–222° C. |
| (ft) | $CH_3$ | 6-F-2-$CF_3$-4-quinolinyl | 254–255° C. |
| (fu) | $CH_3$ | 1-F,3-Cl-2-naphthyl | 158–160° C. |
| (fv) | $CH_3CH_2$ | 3-Cl-2-naphthyl | 154–156° C. |
| (fw) | Cl | 1-Cl,6-F-2-naphthyl | 176–178° C. |
| (fx) | Cl | 1-F,3-Cl-2-naphthyl | 200–202° C. |
| (fy) | $CH_3$ | 1-Cl,3-F-2-naphthyl | 132–134° C. |
| (fz) | $CH_3$ | 1,3-di-F-2-naphthyl | 154–156° C. |
| (ga) | Cl | 1,3-di-F-2-naphthyl | 152–154° C. |
| (gb) | $CH_3CH_2$ | 3-cyclopropyl-2-F,4-$CH_3$,6-Cl-phenyl | 117–119° C. |
| (gc) | Cl | 3-cyclopropyl-2-F,4-$CH_3$,6-Cl-phenyl | 150–154° C. |
| (gd) | cyclopropyl | 4-cyclopropyl-2-Cl,3,5-di-F-phenyl | 139–140° C. |
| (ge) | $CH_3$ | 4-cyclopropyl-2-Cl,5-$CH_3$-phenyl | 114–116° C. |
| (gf) | Cl | 4-cyclopropyl-2-Cl-5-$CH_3$-phenyl | 139–140CC |
| (gg) | $CH_3CH_2$ | 4-cyclopropyl-2-Cl-5-$CH_3$-phenyl | 133–134° C. |
| (gh) | cyclopropyl | 4-cyclopropyl-2-Cl,5-$CH_3$-phenyl | 85–90° C. |
| (gi) | cyclopropyl | 4-cyclopropyl-2-F,3-$CH_3$,6-Cl-phenyl | 121–124° C. |
| (gj) | $CH_3$ | 4-cyclopropyl-2-Cl,3,5-di-F-phenyl | 90–92° C. |
| (gk) | $CH_3CH_2$ | 4-cyclopropyl-2-Cl,3,5-di-F-phenyl | 116–117° C. |
| (gl) | Cl | 4-cyclopropyl-2-Cl,3,5-di-F-phenyl | 64–65° C. |

Example 5

Carboxymethyl 2-(6-chloro-5-indanylamino)phenylacetate

Similarly to procedure described in U.S. Pat. No. 5,291,523,2-(6-chloro-5-indanylamino)phenylacetic acid is converted to the sodium salt and reacted with benzyl 2-bromoacetate to obtain benzyloxycarbonylmethyl 2-(6-chloro-5-indanylamino)phenylacetate which is hydrogenolyzed to carboxymethyl 2-(6-chloro-5-indanylamino)phenylacetate, m.p. 97–100° C.

What is claimed is:

1. A compound of formula (I)

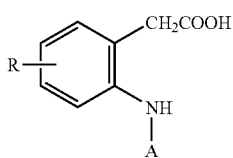

(I)

wherein

R is hydrogen, lower alkyl, ($C_3$–$C_6$)cycloalkyl, hydroxy, halo, lower alkoxy, trifluoromethoxy, trifluoromethyl or cyano; and A is biaryl, optionally substituted β-naphthyl, bicyclic heterocyclic aryl, ($C_3$–$C_6$)cycloalkyl-monocyclic carbocyclic aryl, optionally substituted 5,6,7,8-tetrahydronaphthyl or optionally substituted indanyl; provided that when bicyclic heterocyclic aryl is optionally substituted quinolinyl, R is located at the 5-position and R does not represent hydrogen;

or a pharmaceutically acceptable salt thereof; or a pharmaceutically acceptable ester thereof.

2. A compound according to claim 1, wherein A represents optionally substituted β-naphthyl, optionally substituted quinolinyl, optionally substituted isoquinolinyl, optionally substituted 5,6,7,8-tetrahydronaphthyl, optionally substituted indanyl, optionally substituted biphenylyl, optionally substituted ($C_3$–$C_6$)cycloalkyl-phenyl or optionally substituted monocyclic heteroaryl-phenyl; provided that when A is optionally substituted quinolinyl, R is located at the 5-position and R does not represent hydrogen.

3. A compound according to claim 1 of formula (II)

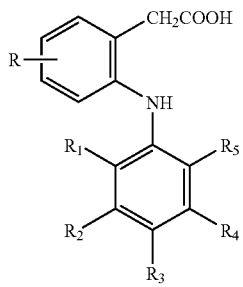

wherein
R is hydrogen, (C$_1$–C$_4$)alkyl, (C$_3$–C$_6$)cycloalkyl, halo, lower alkoxy, trifluoromethoxy, cyano or trifluoromethyl;
R$_1$ is hydrogen, fluoro, chloro, (C$_1$ or C$_2$)alkyl or trifluoromethyl;
R$_2$ is hydrogen, fluoro, chloro, (C$_1$ or C$_2$)alkyl or trifluoromethyl;
R$_3$ is optionally substituted phenyl or (C$_3$–C$_6$)cycloalkyl;
R$_4$ is hydrogen, halo, lower alkyl or trifluoromethyl; and
R$_5$ is halo, lower alkyl or trifluoromethyl;
or a pharmaceutically acceptable salt thereof; or a pharmaceutically acceptable ester thereof.

4. A compound according to claim 3 of formula (II), wherein
R is hydrogen, methyl, ethyl, propyl, methoxy, chloro, fluoro, cyclopropyl, cyano, trifluoromethoxy or trifluoromethyl;
R$_1$, R$_2$, R$_4$ and R$_5$ are, independently, hydrogen, fluoro or chloro; and
R$_3$ is (C$_3$–C$_6$)cycloalkyl, phenyl, or phenyl mono- or poly-substituted independently by lower alkyl, fluoro, chloro, lower alkoxy or (C$_1$ or C$_2$)alkylenedioxy;
or a pharmaceutically acceptable salt thereof; or a pharmaceutically acceptable ester thereof.

5. A compound according to claim 1 of formula (III)

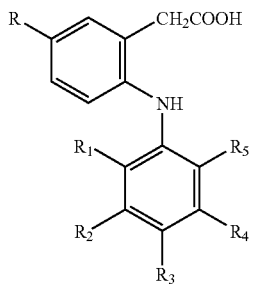

wherein
R is hydrogen, (C$_1$–C$_4$)alkyl, (C$_3$–C$_6$)cycloalkyl, halo, lower alkoxy, trifluoromethoxy or trifluoromethyl;
R$_1$ is hydrogen, chloro, fluoro or (C$_1$ or C$_2$)alkyl;
R$_2$ is hydrogen or fluoro;
R$_3$ is cyclopropyl, cyclohexyl, phenyl or phenyl substituted by chloro, fluoro, lower alkoxy, lower alkyl or lower alkylenedioxy;
R$_4$ is hydrogen, (C$_1$ or C$_2$)alkyl, trifluoromethyl or fluoro; and
R$_5$ is fluoro, chloro or (C$_1$ or C$_2$)alkyl;
or a pharmaceutically acceptable salt thereof; or a pharmaceutically acceptable ester thereof.

6. A compound according to claim 5,
wherein
R is (C$_1$ or C$_2$)alkyl, cyclopropyl, chloro or fluoro;
R$_1$ is chloro or fluoro;
R$_2$ is hydrogen or fluoro;
R$_3$ is cyclopropyl;
R$_4$ is hydrogen, methyl or fluoro; and
R$_5$ is fluoro;
or a pharmaceutically acceptable salt thereof; or a pharmaceutically acceptable ester thereof.

7. A compound according to claim 1 of formula (I), wherein
R is hydrogen, lower alkyl, (C$_3$–C$_6$)cycloalkyl, halo, lower alkoxy, trifluoromethoxy, cyano or trifluoromethyl; and
A is selected from radicals (a) and (b)

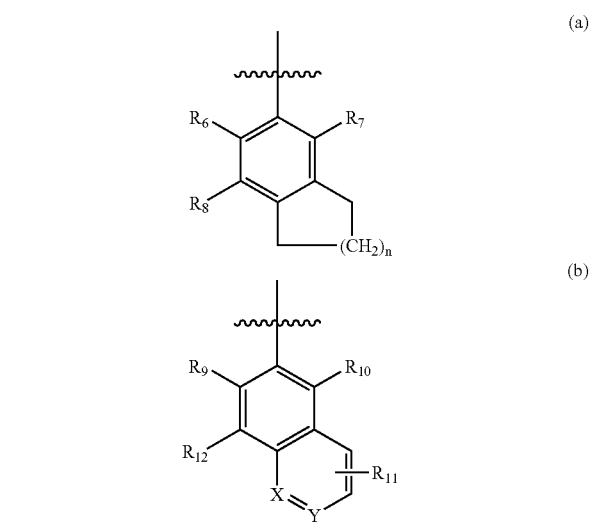

wherein in radical (a)
n is 1 or 2; and
R$_6$–R$_8$ are independently hydrogen, lower alkyl or halo; and
wherein in radical (b)
R$_9$–R$_{12}$ are independently hydrogen, lower alkyl or halo; and
X and Y are CH, or one of the X and Y is N and the other is CH; provided that when X is N and Y is CH, R is located at the 5-position and R does not represent hydrogen;
or a pharmaceutically acceptable salt thereof; or a pharmaceutically acceptable ester thereof.

8. A compound according to claim 1 of formula (Ia)

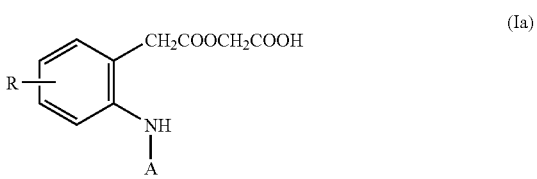

wherein R and A have meaning as defined in said claim; or a pharmaceutically acceptable salt thereof.

9. A pharmaceutical composition comprising an effective amount of a compound of claim 1 in combination with one or more pharmaceutically acceptable carriers.

10. A method for the preparation of a compound of formula (I) of claim 1 which comprises:

a) coupling a compound of formula (IV) or (IVa)

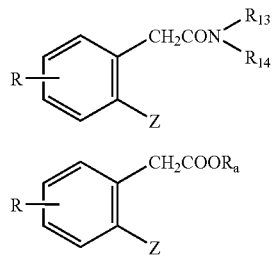

(IV)

(IVa)

wherein
- Z is iodo or bromo;
- R has meaning as defined in claim 1;
- $R_a$ is hydrogen, an alkali metal cation or lower alkyl, preferably isopropyl; and
- $R_{13}$ and $R_{14}$ are lower alkyl; or $R_{13}$ and $R_{14}$ together with the nitrogen atom represent piperidino, pyrrolidino or morpholino;

with a compound of formula (V)

$$A\text{—}NH_2 \quad (V)$$

wherein A has meaning as defined in claim 1, in the presence of copper and cuprous iodide to obtain a compound of formula (VI) or (VIa)

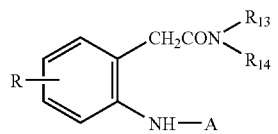

(VI)

-continued

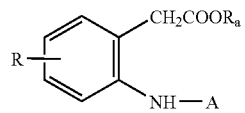

(VIa)

and hydrolyzing the resulting compound of formula (VI) or (VIa) to a compound of formula (I); or b) hydrolyzing a lactam of formula (IX)

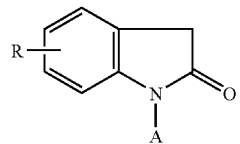

(IX)

wherein
- R and A have meaning as defined in claim 1, with a strong base; and
- in above processes, if desired, temporarily protecting any interfering reactive groups and then isolating the resulting compound of the invention; and, if desired, converting any resulting compound into another compound of the invention; and/or if desired converting a free carboxylic acid of the invention into a pharmaceutically acceptable ester derivative thereof; and/or if desired, converting a resulting free acid into a salt or a resulting salt into the free acid or into another salt.

* * * * *